US012741967B2

(12) United States Patent
Yonemura et al.

(10) Patent No.: US 12,741,967 B2
(45) Date of Patent: Sep. 22, 2026

(54) CONDENSED HETEROCYCLIC COMPOUND HAVING A SULFONAMIDE GROUP OR SALT THEREOF, AGRICULTURAL OR HORTICULTURAL INSECTICIDE OR ANIMAL ECTOPARASITE OR ENDOPARASITE CONTROL AGENT COMPRISING THE COMPOUND OR THE SALT THEREOF, AND METHOD FOR USING THE COMPOUND OR THE SALT THEREOF, THE INSECTICIDE, OR THE CONTROL AGENT

(71) Applicant: NIHON NOHYAKU CO., LTD., Tokyo (JP)

(72) Inventors: Ikki Yonemura, Osaka (JP); Yutaka Abe, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 343 days.

(21) Appl. No.: 18/279,243

(22) PCT Filed: Feb. 28, 2022

(86) PCT No.: PCT/JP2022/008282

§ 371 (c)(1),
(2) Date: Aug. 29, 2023

(87) PCT Pub. No.: WO2022/186133

PCT Pub. Date: Sep. 9, 2022

(65) Prior Publication Data

US 2024/0199600 A1 Jun. 20, 2024

(30) Foreign Application Priority Data

Mar. 1, 2021 (JP) ................................ 2021-031437

(51) Int. Cl.

| | |
|---|---|
| ***C07D 471/04*** | (2006.01) |
| ***A01N 43/90*** | (2006.01) |
| ***A01P 7/04*** | (2006.01) |
| ***C07D 401/04*** | (2006.01) |
| ***C07D 487/04*** | (2006.01) |

(52) U.S. Cl.

CPC .......... *C07D 471/04* (2013.01); *A01N 43/90* (2013.01); *A01P 7/04* (2021.08); *C07D 401/04* (2013.01); *C07D 487/04* (2013.01)

(58) Field of Classification Search

CPC .. C07D 471/04; C07D 401/04; C07D 487/04; C07D 401/14; C07D 413/04; C07D 498/04; A01N 43/90; A01N 43/52; A01N 43/76; C07F 7/0812

See application file for complete search history.

(56) References Cited

U.S. PATENT DOCUMENTS

| | | | |
|---|---|---|---|
| 5,254,799 | A | 10/1993 | De Greve et al. |
| 5,317,096 | A | 5/1994 | De Greve et al. |
| 5,407,454 | A | 4/1995 | Cavalieri et al. |
| 5,530,195 | A | 6/1996 | Kramer et al. |
| 5,545,565 | A | 8/1996 | De Greve et al. |
| 5,625,136 | A | 4/1997 | Koziel et al. |
| 5,760,181 | A | 6/1998 | De Greve et al. |
| 5,767,372 | A | 6/1998 | De Greve et al. |
| 5,843,898 | A | 12/1998 | De Greve et al. |
| 5,859,336 | A | 1/1999 | Koziel et al. |
| 6,018,104 | A | 1/2000 | Koziel et al. |

(Continued)

FOREIGN PATENT DOCUMENTS

| | | |
|---|---|---|
| CN | 107428759 | 12/2017 |
| CN | 110114354 | 8/2019 |

(Continued)

OTHER PUBLICATIONS

Extended European Search Report issued Jan. 20, 2025 in European Patent Application No. 22763189.2.

(Continued)

*Primary Examiner* — Sahar Javanmard

(74) *Attorney, Agent, or Firm* — Wenderoth, Lind & Ponack, L.L.P.

(57) ABSTRACT

An object of the present invention is to provide a novel agricultural or horticultural insecticide and a novel animal ectoparasite or endoparasite control agent in order to solve problems in crop production in the fields of agriculture, horticulture and the like, such as immense damage caused by insect pests, etc. and the emergence of insecticide-resistant pests. The object can be achieved by a condensed heterocyclic compound having a sulfonamide group represented by the general formula (1):

[Chem. 1]

(1)

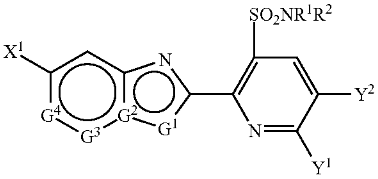

or a salt thereof, an agricultural or horticultural insecticide containing the compound or the salt thereof as an active ingredient, an animal ectoparasite or endoparasite control agent containing the compound or the salt thereof as an active ingredient, and a method for using the compound or the salt thereof, the insecticide, or the control agent.

9 Claims, No Drawings

(56) References Cited

U.S. PATENT DOCUMENTS

| | | | |
|---|---|---|---|
| 6,051,760 | A | 4/2000 | Koziel et al. |
| 6,075,185 | A | 6/2000 | Koziel et al. |
| 6,107,546 | A | 8/2000 | De Greve et al. |
| 6,121,014 | A | 9/2000 | Koziel et al. |
| 6,320,100 | B1 | 11/2001 | Koziel et al. |
| 6,403,865 | B1 | 6/2002 | Koziel et al. |
| 6,689,356 | B1 | 2/2004 | Zlotkin et al. |
| 6,720,488 | B2 | 4/2004 | Koziel et al. |
| 10,266,552 | B2 | 4/2019 | Yonemura et al. |
| 10,544,148 | B2 | 1/2020 | Edmunds et al. |
| 10,654,845 | B2 | 5/2020 | Fischer et al. |
| 10,844,016 | B2 | 11/2020 | Werner et al. |
| 10,856,548 | B2 | 12/2020 | Yonemura et al. |
| 10,939,682 | B2 | 3/2021 | Edmunds et al. |
| 11,229,208 | B2 | 1/2022 | Edmunds et al. |
| 11,524,938 | B2 | 12/2022 | Werner et al. |
| 11,655,258 | B2 | 5/2023 | Hager et al. |
| 2003/0046726 | A1 | 3/2003 | Koziel et al. |
| 2003/0237117 | A1 | 12/2003 | Koziel et al. |
| 2006/0021095 | A1 | 1/2006 | Koziel et al. |
| 2006/0117407 | A1 | 6/2006 | Koziel et al. |
| 2016/0255837 | A1 | 9/2016 | Edmunds et al. |
| 2017/0073342 | A1 | 3/2017 | Fischer et al. |
| 2017/0240554 | A1 | 8/2017 | Edmunds et al. |
| 2018/0002345 | A1 | 1/2018 | Fischer et al. |
| 2018/0002347 | A1 | 1/2018 | Yonemura et al. |
| 2018/0016273 | A1 | 1/2018 | Fischer et al. |
| 2018/0271099 | A1 | 9/2018 | Fischer et al. |
| 2018/0305353 | A1 | 10/2018 | Fischer et al. |
| 2019/0119210 | A1 | 4/2019 | Werner et al. |
| 2020/0085054 | A1 | 3/2020 | Yonemura et al. |
| 2020/0181172 | A1 | 6/2020 | Hager et al. |
| 2021/0037827 | A1 | 2/2021 | Edmunds et al. |
| 2021/0214336 | A1 | 7/2021 | McKerrall et al. |
| 2022/0104496 | A1 | 4/2022 | Edmunds et al. |
| 2022/0324807 | A1 | 10/2022 | Werner et al. |

FOREIGN PATENT DOCUMENTS

| | | |
|---|---|---|
| EP | 0 374 753 | 6/1990 |
| EP | 0 427 529 | 5/1991 |
| EP | 0 451 878 | 10/1991 |
| JP | 2017-512191 | 5/2017 |
| JP | 2018-505881 | 3/2018 |
| JP | 2018-523664 | 8/2018 |
| JP | 2018-536639 | 12/2018 |
| WO | 93/07278 | 4/1993 |
| WO | 95/034656 | 12/1995 |
| WO | 03/052073 | 6/2003 |
| WO | 2012/087938 | 6/2012 |
| WO | 2015/000715 | 1/2015 |
| WO | 2016/059145 | 4/2016 |
| WO | 2016/121997 | 8/2016 |
| WO | 2016/121998 | 8/2016 |
| WO | 2017/191000 | 11/2017 |
| WO | 2018/108726 | 6/2018 |
| WO | 2019/038195 | 2/2019 |
| WO | 2019/226687 | 11/2019 |

OTHER PUBLICATIONS

International Preliminary Report on Patentability issued Aug. 29, 2023 in International (PCT) Application No. PCT/JP2022/008282, with English Translation.

Written Opinion of the International Searching Authority issued Apr. 26, 2022 in International (PCT) Application No. PCT/JP2022/008282.

International Search Report issued Apr. 26, 2022 in International (PCT) Application No. PCT/JP2022/008282.

Parker et al., "Dominant mutations causing alterations in acetyl-coenzyme A carboxylase confer tolerance to cyclohexanedione and aryloxyphenoxypropionate herbicides in maize", Proceedings of the national academy of sciences of the United States of America, 1990, vol. 87, pp. 7175-7179.

Délye, "Weed resistance to acetyl coenzyme A carboxylase inhibitors: an update", Weed Science, 2005, vol. 53, issue 5, Abstract.

Gura , "Repairing the Genome's Spelling Mistakes", 1999, Repairing the genome's spelling mistakes, Science, vol. 285, pp. 316-318.

CONDENSED HETEROCYCLIC COMPOUND HAVING A SULFONAMIDE GROUP OR SALT THEREOF, AGRICULTURAL OR HORTICULTURAL INSECTICIDE OR ANIMAL ECTOPARASITE OR ENDOPARASITE CONTROL AGENT COMPRISING THE COMPOUND OR THE SALT THEREOF, AND METHOD FOR USING THE COMPOUND OR THE SALT THEREOF, THE INSECTICIDE, OR THE CONTROL AGENT

TECHNICAL FIELD

The present invention relates to a condensed heterocyclic compound having a sulfonarnide group or a salt thereof, an agricultural or horticultural insecticide or an animal ectoparasite or endoparasite control agent comprising the compound or the salt thereof as an active ingredient, and a method for using the compound or the salt thereof, the insecticide, or the control agent.

BACKGROUND ART

Certain kinds of condensed heterocyclic compounds having a sulfonamide group have been reported to be useful as pharmaceuticals, insecticides, etc. (e.g., see Patent Literature 1 to 4). However, the literature does not describe any condensed heterocyclic compound which has a nitrogen-containing heterocyclic ring bound at the C2 position and a sulfonamide group bound at the C3 position of the pyridine ring, nor does it describe its insecticidal effect, CITATION LIST

PATENT LITERATURE

Patent Literature 1: WO 2019/226687
Patent Literature 2: WO 2017/191000
Patent Literature 3: WO 2012/087938
Patent Literature 4: WO 2015/000715

SUMMARY OF INVENTION

Technical Problem

In crop production in the fields of agriculture, horticulture and the like, the damage caused by insect pests, etc. is still immense. For addressing the emergence of insecticide-resistant pests, the impact on bioindicators, operational labor saving, etc. there is a need to develop agricultural or horticultural insecticides or animal ectoparasie or endoparasite control agents which have a novel action with less impact on natural predatory and useful insects and exhibit translaminar efficacy.

Solution to Problem

After extensive research to solve the above-mentioned problems, the present inventors found that the problems can be solved by the condensed heterocyclic compound having a sulfonamide group represented by the general formula (I) or a salt thereof, which is highly effective for controlling agricultural or horticultural pests and ectoparasites or endop arasites of animals. Based on this finding, the present inventors completed the present invention.

That is, the present invention includes the following.

[1] A condensed heterocyclic compound having a sulfonamide group represented by the general formula (1):

[Chem. 1]

(1)

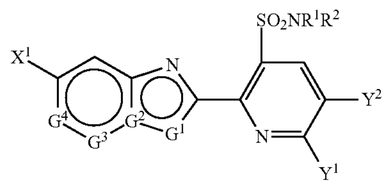

{wherein $R^1$ and $R^2$ may be the same or different and each represent (a1) a hydrogen atom; or (a2) a $(C_1-C_6)$ alkyl group; or (a3) $R^1$ and $R^2$ may join together to form a 3- to 6-membered aliphatic ring having the nitrogen atom of the sulfonamide group, $X^1$ represents (b1) a hydrogen atom;

(b2) a halo $(C_1-C_6)$ alkyl group;

(b3) a halo $(C_1-C_6)$ alkoxy group;

(b4) a halo $(C_1-C_6)$ alkylthio group;

(b5) a halo $(C_1-C_6)$ alkylsulfinyl group; or (b6) a halo $(C_1-C_6)$ alkylsulfonyl group, Y1 represents (c1) a hydrogen atom;

(c2) a halogen atom;

(c3) a $(C_1-C_6)$ alkyl group;

(c4) a $(C_3-C_6)$ cycloalkyl group;

(c5) a cyano $(C_3-C_6)$ cycloalkyl group;

(c6) an aryl group;

(c7) an aryl group having, on the ring, 1 to 5 substituting groups which may be the same or different and are selected from (a) a halogen atom, (b) a cyano group, (c) a nitro group, (d) a (C1-C6) alkyl group, (e) a halo $(C_1-C_6)$ alkyl group, (f) a $(C_1-C_6)$ alkoxy group, (g) a halo (C1-C6) alkoxy group, (h) a $(C_1-C_6)$ alkylthio group, (i) a halo $(C_1-C_6)$ alkylthio group, (j) a (C1-C6) alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group; or (c8) a triazole group, Y2 represents (d1) a hydrogen atom;

(d2) a $(C_3-C_6)$ cycloalkyl group;

(d3) a cyano $(C_3-C_6)$ cycloalkyl group;

(d4) a halo $(C_1-C_6)$ alkyl group;

(d5) a C $(R^3)$-$NOR^4$ group wherein $R^3$ represents a $(C_3-C_6)$ cycloalkyl group, and $R^4$ represents a halo $(C_1-C_6)$ alkyl group;

(d6) an aryl group;

(d7) an aryl group having, on the ring, 1 to 5 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, (m) a halo $(C_1-C_6)$ alkylsulfonyl group, (k) a $(C_1-C_6)$ alkylthio group, (1) a formyl group, (m) a $(C_1-C_6)$ alkylcarbonyl group, (n) a $(C_1-C_6)$ alkoxycarbonyl group, (o) an acetamide group, (p) a methylene dioxy group, and (q) a trimethylsilyl group;

(d8) Y1 and Y2 may join together with the pyridine ring bound to Y1 and Y2 to form an aromatic heterocyclic ring in which the aromatic ring moiety is an aromatic heterocyclic group optionally having, on the ring, 1 to 4 substituting groups selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d9) a halogen atom;

(d10) a $(C_1-C_6)$ alkyl group;

(d11) a $(C_2-C_6)$ alkenyl group;

(d12) a $(C_1-C_6)$ alkoxy group;

(d13) a halo $(C_1-C_6)$ alkoxy group;

(d14) a $(C_1-C_6)$ alkylthio group;

(d15) a $(C_1-C_6)$ alkylsulfonyl group;

(d16) a carboxyl group;

(d17) a $(C_1-C_6)$ alkoxycarbonyl group;

(d18) a cyano $(C_1-C_6)$ alkyl group;

(d19) a cyano halo $(C_1-C_6)$ alkyl group;

(d20) a $(C_1-C_6)$ alkoxy $(C-C_6)$ alkyl group;

(d21) a $(C_1-C_6)$ alkylsulfonyl $(C_1-C_6)$ alkyl group;

(d22) an $NR^aR^b$ group wherein $R^a$ and $R^b$ may be the same or different and each represent (aa) a hydrogen atom, (ab) a $(C-C_6)$ alkyl group, (ac) a $(C_2-C_6)$ alkynyl group, (ad) a $(C_3-C_6)$ cycloalkyl $(C_1-C_6)$ alkyl group, (ae) a $(C_1-C_6)$ alkoxy $(C_1-C_6)$ alkyl group, (af) a $(C_1-C_6)$ alkylcarbonyl group, (ag) a $(C_1-C_6)$ alkoxycarbonyl group, or (ah) a dimethylaminocarbonyl group;

(d23) a $CONR^aR^b$ group wherein $R^a$ and $R^b$ are the same as above;

(d24) a dimethylamino $(C_1-C_6)$ alkylideneamino group;

(d25) a dimethylsulfinylideneamino group;

(d26) a pyrimidyl group;

(d27) a pyrimidyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d28) a pyridyl group;

(d29) a pyridyl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d30) a pyridazinyl group;

(d31) a pyridazinyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d32) a pyrazinyl group;

(d33) a pyrazinyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d34) a furanyl group;

(d35) a furanyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d36) a thienyl group;

(d37) a thienyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group; (d38) an imidazole group;

(d39) an imidazole group having, on the ring, 1 or 2 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d40) a pyrazole group;

(d41) a pyrazole group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d42) a thiazole group;

(d43) a thiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d44) an isothiazole group;

(d45) an isothiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d46) an oxazole group;

(d47) an oxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d48) an isoxazole group;

(d49) an isoxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d50) an oxadiazole group;

(d51) an oxadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d52) a thiadiazole group;

(d53) a thiadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio: group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d54) a triazole group;

(d55) a triazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d56) a pyrimidyloxy group;

(d57) a pyridyloxy group; or the following structural formula $Q^1$, $Q^2$, $Q^3$, $Q^4$, $Q^5$, or $Q_6$:

[Chem. 2]

$Q^1$

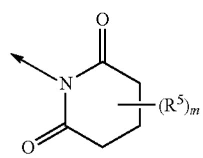

$Q^2$

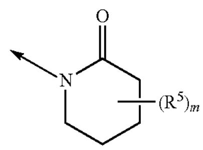

$Q^3$

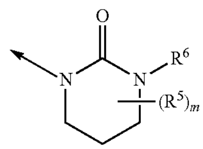

$Q^4$

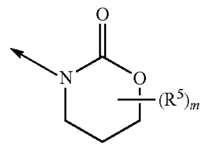

$Q^5$

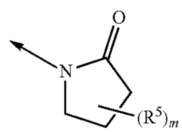

$Q^6$

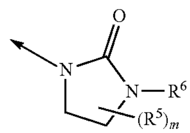

wherein $R^5$s may be the same or different and each represent a halogen atom or a ($C_1$-$C_6$) alkyl group; $R^6$ represents a ($C_1$-$C_6$) alkyl group; m represents an integer of 0 to 2, and the arrow represents a binding position, $G^1$ represents an oxygen atom, a nitrogen atom, CH, CF, or N—$CH_3$, $G^2$ represents a carbon atom or a nitrogen atom, $G^3$ represents a nitrogen atom or CH, and $G^4$ represents a nitrogen atom or a C—$X^2$ group (wherein $X^2$ represents a hydrogen atom or a halo ($C_1$-$C_6$) alkyl group)}, or a salt thereof.

[2] The condensed heterocyclic compound having a sulfonamide group or the salt thereof according to the above [1], wherein $R^1$ and $R^2$ may be the same or different and each represent (a1) a hydrogen atom; or (a2) a ($C_1$-$C_6$) alkyl group; or (a3) $R^1$ and $R^2$ may join together to form a 3- to 6-membered aliphatic ring having the nitrogen atom of the sulfonamide group, $X^1$ represents (b1) a hydrogen atom;

(b2) a halo ($C_1$-$C_6$) alkyl group;

(b3) a halo ($C_1$-$C_6$) alkoxy group;

(b4) a halo ($C_1$-$C_6$) alkylthio group;

(b5) a halo ($C_1$-$C_6$) alkylsulfinyl group; or (b6) a halo ($C_1$-$C_6$) alkylsulfonyl group, $Y^1$ represents (c1) a hydrogen atom;

(c2) a halogen atom;

(3) a ($C_3$-$C_6$) alkyl group;

(c4) a ($C_3$-$C_6$) cycloalkyl group;

(c5) a cyano ($C_3$-$C_6$) cycloalkyl group;

(c7) an aryl group having, on the ring, 1 to 5 substituting groups which may be the same or different and are selected from (a) a. halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_5$) alkylsulfinyl group, (1) a ($C_1$-$C_6$) alkylsulfonyl group, and (m) a halo ($C_1$-$C_6$) alkylsulfonyl group; or (c8) a triazole group, $Y^2$ represents (d1) a hydrogen atom;

(d2) a ($C_3$-$C_6$) cycloalkyl group;

(d3) a cyano ($C_3$-$C_6$) cycloalkyl group;

(d4) a halo ($C_1$-$C_6$) alkyl group;

(d5) a $C(R^3)$=:$NOR^4$ group wherein $R^3$ represents a ($C_3$-$C_6$) cycloalkyl group, and $R^4$ represents a halo ($C_1$-$C_6$) alkyl group;

(d7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_3$-$C_6$) alkyl group, (f) a ($C_J$-$C_c$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_5$) alkylsulfinyl group, (k) a halo ($C_1$-$C_5$) alkylsulfinyl group, (1) a ($C_1$-$C_6$) alkylsulfonyl group, (m) a halo ($C_1$-$C_6$) alkylsulfonyl group, (k) a ($C_1$-$C_6$) alkylthio group, (1) a formyl group, (m) a ($C_1$-$C_6$) alkylcarbonyl group, (n) a ($C_1$-$C_6$) alkoxycarbonyl group, (o) an acetamide group, (p) a methylene dioxy group, and (q) a trimethylsilyl group;

(d8) $Y^1$ and Y, may join together with the pyridine ring bound to $Y^1$ and $Y^2$ to form an aromatic heterocyclic ring in which the aromatic ring moiety is an aromatic heterocyclic group optionally having, on the ring, 1 to 4 substituting groups selected from (a) a halogen atom, (b) a cyano group, (c) a nitro group, (d) a ($C_1$-$C_6$) alkyl group, (e) a halo ($C_1$-$C_6$) alkyl group, (f) a ($C_3$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, 0) a ($C_1$-$C_6$) alkysulfonyl group, (k) a halo ($C_3$-$C_6$) alkylsulfinyl group, (1) a ($C_1$-$C_6$) alkylsulfonyl group, and (n) a halo ($C_1$-$C_6$) alkylsulfonyl group:

(d9) a halogen atom;

(d10) a ($C_1$-$C_6$) alkyl group;

(d11) a ($C_2$-$C_6$) alkenyl group;

(d12) a ($C_1$-$C_6$) alkoxy group;

(d13) a halo ($C_1$-$C_6$) alkoxy group;

(d14) a ($C_1$-$C_6$) alkylthio group;

(d15) a ($C_1$-$C_6$) alkylsulfonyl group;

(d16) a carboxyl group;

(d17) a ($C_1$-$C_6$) alkoxycarbonyl group;

(d18) a cyano ($C_1$-$C_6$) alkyl group;

(d19) a cyano halo ($C_1$-$C_6$) alkyl group;

(d20) a ($C_1$-$C_6$) alkoxy ($C_1$-$C_6$) alkyl group;

(d21) a ($C_1$-$C_6$) alkylsulfonyl ($C_1$-$C_6$) alkyl group;

(d22) an $NR^aR^b$ group wherein $R^a$ and $R^b$ may be the same or different and each represent (aa) a hydrogen atom, (ab) a ($C_1$-$C_6$) alkyl group, (ac) a ($C_2$-$C_6$) alkynyl group, (ad) a ($C_3$-$C_6$) cycloalkyl ($C_1$-$C_6$) alkyl group, (ae) a ($C_1$-$C_6$) alkoxy ($C_1$-$C_6$) alkyl group, (af) a ($C_1$-$C_6$) alkylcarbonyl group, (ag) a ($C_1$-$C_6$) alkoxycarbonyl group, or (ah) a dimethylaminocarbonyl group;

(d23) a $CONR^aR^b$ group wherein $R^a$ and $R^1$ are the same as above;

(d24) a dimethylamino ($C_1$-$C_6$) alkylideneamino group;

(d25) a dimethylsulfiylideneamino group;

(d26) a pyrimidyl group;

(d27) a pyrinidyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d28) a pyridyl group:

(d29) a pyridyl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (n) a halo ($C_1$-$C_6$) alkylsulfonyl group;

(d30) a pyridazinyl group:

(d31) a pyridazinyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, j) a ($C_1$-$C_6$) alkylsuifinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d32) a pyrazinyl group;

(d33) a pyrazinyl group having, on the ring, 1 to 3 substituting groups which may be the same or different and are selected from (a) a halogen atom, (b) a cyano group, (c) a nitro group, (d) a ($C_1$-$C_6$) alkyl group, (e)

a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d34) a furanyl group;

(d35) a furanyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_5$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d36) a thienyl group;

(d37) a thienyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_5$) alkoxy group, (h) a ($C_1$-$C_6$) alkylthio group, (i) a halo ($C_1$-$C_6$) alkylthio group, (j) a ($C_1$-$C_5$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d38) an imidazole group;

(d39) an imidazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d40) a pyrazole group;

(d41) a pyrazole group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d42) a thiazole group;

(d43) a thiazole group having, on the ring, 1 or 2 substituting groups which may, be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_5$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d44) an isothiazole group;

(d45) an isothiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d46) an oxazole group;

(d47) an oxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d48) an isoxazole group;

(d49) an isoxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d50) an oxadiazole group;

(d51) an oxadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d52) a thiadiazole group;

(d53) a thiadiazole group having, on the ring, one substituting group which may be the same or different and is selected from (a) a halogen atom, (b) a, cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d54) a triazole group;

(d55) a triazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_3$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (n) a halo ($C_1$-$C_6$) alkylsulfonyl group;

(d56) a pyrimidyloxy group; or (d57) a pyridyloxy group, $R^5$s may be the same or different and each represent a halogen atom or a ($C_1$-$C_6$) alkyl group, $R^1$ represents a ($C_1$-$C_6$) alkyl group, in represents an integer of 0 to 2, $G^1$ represents an oxygen atom, a nitrogen atom, CH, or N—$CH_3$, $G^2$ represents a carbon atom or a nitrogen atom, G3 represents a nitrogen atom or CH, and $G^4$ represents a nitrogen atom or a C—$X^2$ group where in $X^2$ is the same as above.

[3] The condensed heterocyclic compound having a sulfonamide group or the salt thereof according to the above [1] or [2], wherein $G^1$ represents N—$CH_3$, $G^2$ represents a carbon atom, $G^3$ represents a nitrogen atom, and $G^4$ represents a C—$X^2$ group wherein $X^2$ is the same as above.

[4] The condensed heterocyclic compound having a sulfonamide group or the salt thereof according to the above [1] or [2], wherein $G^1$ represents a nitrogen atom, $G^2$ represents a carbon atom, and (3 and $G^4$ each represent a nitrogen atom.

[5] The condensed heterocyclic compound having a sulfonamide group or the salt thereof according to the above [1] or [2], wherein $G^1$ represents a nitrogen atom, GP represents a nitrogen atom, $G^3$ represents CH, and $G^4$ represents a C—$X^2$ group wherein $X^2$ is the same as above.

[6] An agricultural or horticultural insecticide comprising the condensed heterocyclic compound having a sulfonamide group or the salt thereof according to any one of the above [1] to [5] as an active ingredient.

[7] A method for using an agricultural or horticultural insecticide, comprising treating plants or soil with an effective amount of the condensed heterocyclic compound having a sulfonamide group or the salt thereof according to any one of the above [1] to [5].

[8] An animal ectoparasite control agent comprising an effective amount of the condensed heterocyclic compound having a sulfonamide group or the salt thereof according to any one of the above [1] to 151 as an active ingredient.

[9] An animal endoparasite control agent comprising an effective amount of the condensed heterocyclic compound having a sulfonamide group or the salt thereof according to any one of the above [1] to [5] as an active ingredient.

Advantageous Effects of Invention

The condensed heterocyclic compound having a sulfonamide group of the present invention or a salt thereof is not only a highly effective agricultural or horticultural insecticide but also is effective against pests which live on pet animals such as dogs and cats and domestic animals such as cattle and sheep.

DESCRIPTION OF EMBODIMENTS

In the definition of the general formula (1) representing the condensed heterocyclic compound having a sulfonamide group of the present invention or a salt thereof, "halo" refers to a "halogen atom" and represents a fluorine atom, a chlorine atom, a bromine atom, or an iodine atom.

The "($C_1$-$C_6$) alkyl group" refers to a straight-chain or branched-chain alkyl group of 1 to 6 carbon atoms, for example, a methyl group, an ethyl group, a n-propyl group, an isopropyl group, a, n-butyl group, an isobutyl group, a sec-butyl group, a, tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a. 3-methylpentyl group, a 1,1,2-trimethyl propyl group, a 3,3-dimethylbutyl group or the like. The "($C_2$-$C_6$) alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "($C_2$-$C_6$) alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "($C_3$-$C_6$) cycloalkyl group" refers to a cyclic alkyl group of 3 to 6 carbon atoms, for example, a cyclopropyl group, a cyclobutyl group, a cyclopentyl group, a cyclohexyl group or the like. The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a, tert-butylthio group, a, n-pentylthio group, an isopentylthio group, a, tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like. The "($C_1$-$C_5$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, an-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like. The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutyisulfonyl group, a n-hexylsulfony 1 group, an isohexylsulfonyl group, a 1,1,2-trimethylpropylsulfonyl group or the like.

The above-mentioned "($C_1$-$C_6$)(j) alkyl group", "($C_1$-$C_6$) cycloalkyl group", "($C_1$-$C_6$) alkoxy group", "($C_1$-$C_6$) alkylthio group", "($C_1$-$C_6$) alkylsulfinyl group", and "($C_1$-$C_6$) alkylsulfonyl group", may be substituted with one or more halogen atoms at a substitutable position(s), and in the case where any of the above-listed groups is substituted with two or more halogen atoms, the halogen atoms may be the same or different. The above-mentioned groups substituted with one or more halogen atoms are expressed as a "halo ($C_3$-$C_6$) alkyl group", a "halo ($C_2$-$C_6$) alkenyl group", a "halo ($C_2$-$C_6$) alkynyl group", a "halo ($C_3$-$C_6$) cycloalkyl group", a "halo ($C_1$-$C_6$) alkoxy group", a "halo ($C_1$-$C_6$) alkylthio group", a "halo ($C_1$-$C_6$) alkylsulfinyl group", and a "halo ($C_1$-$C_6$) alkylsulfonyl group"

The expressions "($C_1$-$C_6$)", "($C_3$-$C_6$)", etc. each represent the range of the number of carbon atoms in each group. The same definition holds true for groups in which two or more of the above-mentioned groups are coupled together, and for example, the "hydroxy ($C_1$-$C_6$) alkyl group" means that a hydroxyl group is bound to a straight-chain or branched-chain alkyl group of 1 to 6 carbon atoms.

The "aryl group" refers to an aromatic hydrocarbon group of 6 to 10 carbon atoms, for example, a phenyl group, a 1-naphthyl group, a 2-naphthyl group or the like.

The "triazole group" refers to, for example, a 1,2,3-triazole group or a 1,2,4-triazole group.

The "oxadiazole group" refers to, for example, a 1,2,4-oxadiazole group or a 1,3,4-oxadiazole group.

The "thiadiazole group" refers to, for example, a 1,2,4-thiadiazole group or a 1,3,4-thiadiazole.

The "($C_1$-$C_6$) alkylcarbonyl group" refers to an alkylcarbonyl group composed of a carbonyl group and a straight-chain or branched-chain alkyl group of 1 to 6 carbon atoms, for example, an acetyl group, a propionyl group, a butyryl group, an isobutyryl group, a n-butylcarbonyl group, an isobutylcarbonyl group, a sec-butylcarbonyl group, a. tert-butylcarbonyl group, a n-pentylcarbonyl group, an isopentylcarbonyl group, a, tert-pentylcarbonyl group, a neopentylcarbonyl group, a 2,3-dimethylpropyicarbonyl group, an 1-ethylpropylcarbonyl group, a 1-methylbutylcarbonyl group, a 2-mnethybutylcarbonyl group, a n-hexylcarbonyl group, an isohexylcarbonyl group, a 2-hexylcarbonyl group, a 3-hexylcarbonyl group, a 2-methylpentylcarbonyl group, a 3-methylpentylearbonyl group, a 1,1,2-trimethylpropylcarbonyl group, a 3,3-dimethylbutylcarbonyl group or the like.

The "($C_1$-$C_6$) alkoxycarbonyl group" refers to an alkoxycarbonyl group composed of a carbonyl group and a straight-chain or branched-chain alkoxy group of 1 to 6 carbon atoms, for example, a methoxycarbonyl group, an ethoxycarbonyl group, a n-propoxycarbonyl group, an isopropoxycarbonyl group, a n-butoxycarbonyl group, a sec-butoxycarbonyl group, a tert-butoxycarbonyl group, a n-pentyloxycarbonyl group, an isopentyloxycarbonyl group, a tert-pentyloxycarbonyl group, a, neopentyloxycarbonyl group, a 2,3-dimeithylpropyloxycarbonyl group, an 1-ethylpropyloxycarbonyl group, a 1-methylbutyloxycarbonyl group, a n-hexyloxycarbonyl group, an isohexyloxycarbonyl group, a 1,1,2-trimethiylpropyloxycarbonyl group or the like. Examples of the "dimethylamino ($C_1$-$C_6$) alkylideneamino group" include a dimethylaminomethyiideneainino group, a dimethylaminoethyihdenearnino group, a dimethylaminopropylideneamino group, a dimethylaminobutylideneamino group, a dimethylaminopentylideneamino group, and dimethylaminohexylideneamino group.

Examples of the 3- to 6-membered aliphatic ring that may be formed by joining R and $R^2$ together with the nitrogen atom of the sulfonamide group include an aziridine ring, an azetidine ring, a pyrrolidine ring, and a piperidine ring.

Examples of the aromatic heterocyclic ring formed by joining $Y^1$ and $Y^2$ together with the pyridine ring bound to $Y^1$ and $Y^2$ include a quinoline ring.

Examples of the salt of the condensed heterocyclic compound having a sulfonamide group represented by the general formula (1) of the present invention include inorganic acid salts, such as hydrochlorides, sulfates, nitrates and phosphates; organic acid salts, such as acetates, fuiriarates, maleates, oxalates, methanesulfonates, benzenesulfonates and p-toluenesulfonates; and salts with an inorganic or organic base such as a sodium ion, a potassium ion, a calcium ion and a trimethylammonium ion.

The condensed heterocyclic compound having a sulfonamide group represented by the general formula (1) of the present invention and a salt thereof can have one or more chiral centers in the structural formula and can exist as two or more kinds of optical isomers or diastereomers. All the optical isomers and mixtures of the isomers at any ratio are also included in the present invention. Further, the condensed heterocyclic compound having a sulfonamide group represented by the general formula (1) of the present invention and a salt thereof can exist as two kinds of geometric isomers due to a carbon-carbon double bond in the structural formula. All the geometric isomers and mixtures of the isomers at any ratio are also included in the present invention.

In a preferable embodiment of the condensed heterocyclic compound having a sulfonamide group represented by the general formula (1) of the present invention or a salt thereof, $R^1$ and $R^2$ are each
(a1) a hydrogen atom: or
(a2) a ($C_1$-$C_6$) alkyl group; or
(a3) $R^1$ and $R^2$ may join together to form a 3- to 6-membered aliphatic ring having the nitrogen atom of the sulfonamide group, $X^1$ is
(b1) a hydrogen atom;
(b2) a halo ($C_1$-$C_6$) alkyl group;
(b3) a halo ($C_1$-$C_6$) alkoxy group;
(b4) a halo ($C_1$-$C_6$) alkylthio group;
(b5) a halo ($C_1$-$C_6$) alkylsulfinyl group; or
(b6) a halo ($C_1$-$C_6$) alkylsulfonyl group, $Y^2$ is
(c1) a hydrogen atom;
(c2) a halogen atom;
(c3) a ($C_1$-$C_6$) alkyl group;
(c4) a ($C_3$-$C_6$) cycloalkyl group;
(c5) a cyano ($C_3$-$C_6$) cycloalkyl group;
(c7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group; or
(c8) a triazole group, $Y^2$ is
(d1) a hydrogen atom;
(d2) a ($C_1$-$C_6$) cycloalkyl group;
(d3) a cyano ($C_5$-$C_6$) cycloalkyl group;
(d4) a halo ($C_1$-$C_6$) alkyl group;
(d5) a $C(R^3)$=$NO^4$ group wherein $R^3$ represents a ($C_3$-$C_6$) cycloalkyl group, and $R^4$ represents a halo ($C_1$-$C_6$) alkyl group;
(d7) an aryl group having, on the ring, 1 to 5 substituting groups which may be the same or different and are selected from (a) a halogen atom, (b) a cyano group, (c)

a nitro group, (d) a $(C_1-C_6)$ alkyl group, (e) a halo $(C_1-C_6)$ alkyl group, (f) a $(C_1-C_6)$ alkoxy group, (g) a halo $(C_1-C_5)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, (m) a halo $(C_1-C_6)$ alkylsulfonyl group, (k) a $(C_1-C_6)$ alkylthio group, (1) a formyl group, (m) a $(C_1-C_6)$ alkylcarbonyl group, (n) a $(C_1-C_6)$ alkoxycarbonyl group, (o) an acetamide group, (p) a methylene dioxy group, and (q) a trimethylsilyl group:

(d8) $Y^1$ and $Y^2$ may join together with the pyridine ring bound to $Y^1$ and $Y^1$ to form an aromatic heterocyclic ring in which the aromatic ring moiety is an aromatic heterocyclic group optionally having, on the ring, 1 to 4 substituting groups selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d9) a halogen atom;

(d10) a $(C_1-C_6)$ alkyl group;

(d11) a $(C_2-C_6)$ alkenyl group;

(d12) a $(C_1-C_6)$ alkoxy group;

(d13) a halo $(C_1-C_6)$ alkoxy group;

(d14) a $(C_1-C_5)$ alkylthio group;

(d15) a $(C_1-C_6)$ alkylsulfonyl group;

(d16) a carboxyl group;

(d17) a $(C_1-C_6)$ alkoxycarbonyl group;

(d18) a cyano $(C_1-C_F)$ alkyl group;

(d19) a cyano halo $(C_1-C_6)$ alkyl group;

(d20) a $(C_1-C_6)$ Alkoxy $(C_1-C_6)$ alkyl group;

(d21) a $(C_1-C_6)$ alkylsulfonyl $(C_1-C_6)$ alkyl group;

(d22) an $NR^aR^b$ group wherein $R^1$ and $R^b$ may be the same or different and each represent (aa) a hydrogen atom, (ab) a $(C_1-C_6)$ alkyl group, (ac) a $(C_2-C_6)$ alkynyl group, (ad) a $(C_3-C_6)$ cycloalkyl $(C_1-C_6)$ alkyl group, (ae) a $(C_1-C_6)$ alkoxy $(C_1-C_6)$ alkyl group, (af) a $(C_1-C_6)$ alkylcarbonyl group, (ag) a $(C_1-C_6)$ alkoxycarbonyl group, or (ah) a dimethylaminocarbonyl group;

(d23) a $CONR^aR^b$ group wherein $R^a$ and $R^b$ are the same as above:

(d24) a dimethylamino $(C_1-C_6)$ alkylideneamino group;

(d25) a dimethylsulfinylideneamino group;

(d26) a pyrimidyl group;

(d27) a pyrimidyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfnyl group, (k) a halo $(C_1-C_6)$ alkylsulfinyl group, (I) a $(C_1-C_6)$ alkylsulfonyl group, and (m) a halo $(C_1-C_6)$ alkylsulfonyl group;

(d28) a pyridyl group:

(d29) a pyridyl group having, on the ring, 1 to 4 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d30) a pyridazinyl group;

(d31) a pyridazinyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (l) a $(C_1-C_6)$ alkylsulfonyl group, and (m) a halo $(C_1-C_6)$ alkylsulfonyl group;

(d32) a pyrazinyl group;

(d33) a pyrazinyl group having, on the ring, Ito 3 substituting groups which may be the same or different and are selected from (a) a halogen atom, (b) a cyano group, (c) a nitro group, (d) a $(C_1-C_6)$ alkyl group, (e) a halo $(C_1-C_5)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d34) a furanyl group;

(d35) a furanyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d36) a thienyl group;

(d37) a thienyl group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_6)$ alkylsulfinyl group, (k) a halo $(C_1-C_6)$ alkylsulfinyl group, (1) a $(C_1-C_6)$ alkylsulfonyl group, and (m) a halo $(C_1-C_6)$ alkylsulfonyl group;

(d38) an imidazole group;

(d39) an imidazole group having, on the ring, 1 or 2 substituting groups which may be the same or different and are selected from (a) a halogen atom, (b) a cyano group, (c) a nitro group, (d) a $(C_1-C_5)$ alkyl group, (e) a halo $(C_1-C_6)$ alkyl group, (f) a $(C_1-C_6)$ alkoxy group, (g) a halo $(C_1-C_6)$ alkoxy group, (h) a $(C_1-C_6)$ alkylthio group, (i) a halo $(C_1-C_6)$ alkylthio group, (j) a $(C_1-C_5)$ alkylsulfinyl group, (k) a halo $(C_1-C_5)$ alkylsulfinyl group, (l) a $(C_1-C_6)$ alkylsulfonyl group, and (m) a halo $(C_1-C_6)$ alkylsulfonyl group;

(d40) a pyrazole group;

(d41) a pyrazole group having, on the ring, 1 to 3 substituting groups which may be the same or different and are selected from (a) a halogen atom, (b) a cyano group, (c) a nitro group, (d) a $(C_1-C_6)$ alkyl group, (e) a halo $(C_1-C_6)$ alkyl group, (f) a $(C_1-C_6)$ alkoxy group, (g) a halo ($C_1$-$C_5$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d42) a thiazole group;

(d43) a thiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_5$) alkyl group, (f) a ($C_1$-$C_6$) alkoxy group, (g) a halo ($C_1$-$C_5$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (I) a ($C_1$-$C_6$) alkylsulfonyl group, and (m) a halo ($C_1$-$C_6$) alkylsulfonyl group;

(d44) an isothiazole group;

(d45) an isothiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsuifinyl group, (k) a halo ($C_1$-$C_6$) alkylsulfinyl group, (I) a ($C_1$-$C_6$) alkylsulfonyl group, and (m) a halo ($C_1$-$C_6$) alkylsulfonyl group;

(d46) an oxazole group;

(d47) an oxazole group having, on the ring, 1 or 2 substituting groups which may be the same or different and are selected from (a) a halogen atom, (b) a cyano group, (c) a nitro group, (d) a ($C_1$-$C_6$) alky 1 group, (e) a halo ($C_1$-$C_5$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (l) a ($C_1$-$C_6$) alkylsulfonyl group, and (m) a halo ($C_1$-$C_6$) alkylsulfonyl group;

(d48) an isoxazole group;

(d49) an isoxazole group having, on the ring, 1 or 2 substituting groups which may be the same or different and are selected from (a) a halogen atom, (b) a cyano group, (c) a nitro group, (d) a ($C_1$-$C_5$) alkyl group, (e) a halo ($C_1$-$C_6$) alkyl group, (f) a ($C_1$-$C_5$) alkoxy group, (g) a halo ($C_1$-$C_6$) alkoxy group, (h) a ($C_1$-$C_6$) alkylthio group, (i) a halo ($C_1$-$C_6$) alkylthio group, i) a ($C_1$-$C_6$) alkylsulfinyl group, (k) a halo ($C_1$-$C_6$) alkylsulfinyl group, (I) a ($C_1$-$C_6$) alkylsulfonyl group, and (m) a halo ($C_1$-$C_6$) alkylsulfonyl group;

(d50) an oxadiazole group;

(d51) an oxadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_5$) alkylthio group, (j) a ($C_1$-$C_5$) alkylsulfinyl group, (k) a halo ($C_1$-$C_5$) alkylsulfinyl group, (1) a (($C_1$-$C_6$) alkylsulfonyl group, and (m) a halo ($C_1$-$C_6$) alkylsulfonyl group;

(d52) a thiadiazole group;

(d53) a thiadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_5$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_5$) alkylsulfonyl group, and (m) a halo ($C_1$-$C_6$) alkylsulfonyl group;

(d54) a triazole group;

(d55) a triazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_5$) alkylsulfinyl group, (k) a halo ($C_1$-$C_5$) alkylsulfinyl group, (1) a ($C_1$-$C_{56}$) alkylsulfonyl group, and (m) a halo ($C_1$-$C_6$) alkylsulfonyl group;

(d56) a pyrinidyloxy group; or (d57) a pyridyloxy group, $R^5$s may be the same or different and are each a halogen atom or a ($C_1$-$C_6$) alkyl group, $R^6$ is a ($C_1$-$C_6$) alkyl group, m is an integer of 0 to 2, $G^1$ is an oxygen atom, a nitrogen atom, CH, or N—$CH_3$, $G^2$ is a carbon atom or a nitrogen atom, $G^3$ is a nitrogen atom or CH, and $G^4$ is a nitrogen atom or a C—$X^2$ group wherein $X^2$ is the same as above.

In more preferable embodiments, $G^1$ is N—$CH_3$, $G^2$ is a carbon atom, $G^3$ is a nitrogen atom, and $G^4$ is a C—$X^2$ group wherein $X^2$ is the same as above;

$G^1$ is a nitrogen atom, $G^2$ is a carbon atom, and (P and $G^1$ are each a nitrogen atom; or $G^1$ is a nitrogen atom, $G^2$ is a nitrogen atom, $G^3$ is CH, and (P is a C—$X^2$ group wherein X is the same as above.

The condensed heterocyclic compound having a sulfonamide group represented by the general formula (1) of the present invention or a salt thereof (hereinafter may be abbreviated simply as the condensed heterocyclic compound) can be produced according to, for example, the production method described below, which is a non-limiting example.

Production Method 1

[Chem. 3]

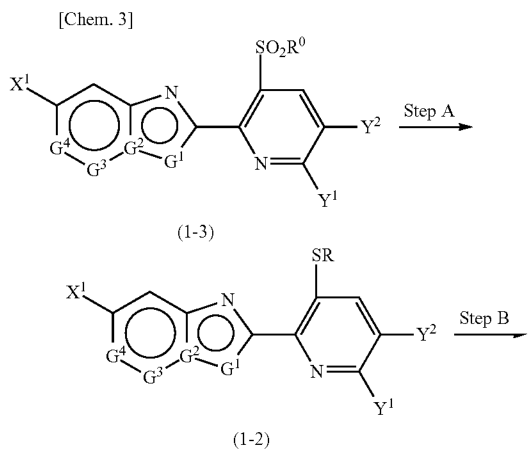

(1-3)

(1-2)

-continued

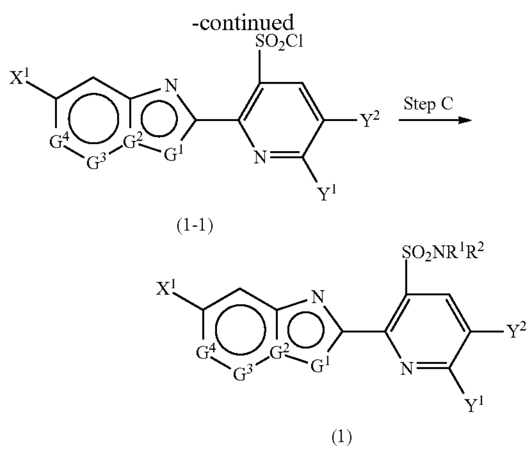

(1-1)

(1)

In the formula, $G^1$, $G^2$, $G^3$, $G^4$, $X^1$, $Y^1$, $Y^2$, $R^1$, and $R^2$ are the same as above, $R^0$ represents a $C_1$-$C_3$ alkyl group, and R represents a benzyl group, a benzyl group substituted with a $C_1$-$C_3$ alkyl group or a $C_1$-$C_3$ alkoxy group, etc.

Production Method at Step [A]

The condensed heterocyclic compound represented by the general formula (1-2) can be produced by reacting the condensed heterocyclic compound represented by the general formula (1-3). which is produced by the method described in WO 2016/059145, WO 2016/121997, WO 2016/121998, or WO 2019/038195, with RSH (wherein R is the same as above) in the presence of a base and an inert solvent.

Examples of the base used in this reaction include inorganic bases such as sodium hydroxide, potassium hydroxide, sodium carbonate, potassium carbonate, sodium hydrogen carbonate, potassium hydrogen carbonate, sodium hydride, and potassium hydride; acetates such as sodium acetate and potassium acetate; alkali metal alkoxides such as potassium t-butoxide, sodium methoxide, and sodium ethoxide; tertiary amines such as triethylamine, diisopropylethylaimine, and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (1-3).

The inert solvent used in this reaction may be any solvent that does not markedly inhibit the progress of the reaction, and examples include aromatic hydrocarbons such as benzene, toluene, and xylene; halogenated aromatic hydrocarbons such as chlorobenzene and dichlorobenzene; chain or cyclic ethers such as diethyl ether, methyl tert-butyl ether, dioxane, and tetrahydrofuran; amides such as dimethylformamide and dimethylacetarnide; ketones such as acetone and methyl ethyl ketone; polar solvents such as dimethyl sulfoxide and 1,3-dimethyl-2-imidazolidinone; and alcohols such as methanol, ethanol, propanol, and isopropyl alcohol. One of these inert solvents may be used alone, and also two or more of them may be used as a mixture.

Since this reaction is an equimolar reaction of the reactants, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. Alternatively, the post-reaction mixture may be directly subjected to the next step without isolation of the condensed heterocyclic compound represented by the general formula (1-2).

Production Method at Step [B]

The condensed heterocyclic compound having a sulfonyl chloride group represented by the general formula (1-1) can be produced by reacting the condensed heterocyclic compound represented by the general formula (1-2) with a chlorinating agent in the presence of an inert solvent.

Examples of the chlorinating agent used in this reaction include chlorine, thionyl chloride, N-chlorosuccinimide, and 1,3-dichloro-5,5-dimethylhydantoin.

The inert solvent used in this reaction may be any solvent that does not markedly inhibit the progress of the reaction, and examples include halogenated hydrocarbons such as methylene chloride, chloroform, and carbon tetrachloride; halogenated aromatic hydrocarbons such as chlorobenzene and dichlorobenzene; nitriles such as acetonitrile and propionitrile; organic acids such as acetic acid and propionic acid; and water. One of these inert solvents may be used alone, and also two or more of them may be used as a mixture.

Since this reaction is an equimolar reaction of the reactants, they are basically used in equimolar amounts. but either of them may be used in an excess amount. The reaction temperature may be in the range of room temperature to the boiling point of the inert solvent used. The reaction time varies, with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of the present invention. Alternatively, the post-reaction mixture may be directly subjected to the next step without isolation of the condensed heterocyclic compound represented by the general formula (1-1).

Production Method at Step [C]

The condensed heterocyclic compound having a sulfonamide group represented by the general formula (1) can be produced by reacting the condensed heterocyclic compound represented by the general formula (1-1) with $NHR^1R^2$ (wherein $R^1$ and $R^2$ are the same as above) in the presence of a base and an inert solvent.

The inert solvent used in this reaction may be any solvent that does not markedly inhibit the progress of the reaction, and examples include aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; chain or cyclic ethers such as diethyl ether, methyl tert-butyl ether, dioxane, and tetrahydrofuran; alcohols such as methanol, ethanol, propanol, and isopropyl alcohol; amides such as dimethylformamide and dimethylacetamide; and polar solvents such as dimethyl sulfoxide and 1,3-dimethyl-2-imidazolidinone. One of these inert solvents may be used alone, and also two or more of them may be used as a mixture.

Since this reaction is an equimolar reaction of the reactants, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of the present invention, Specific examples of the compound of the present invention are shown below. In the following tables, Me stands for a methyl group, Et stands for an ethyl group, c-Pr stands for a cyclopropyl group, i-Pr stands for an isopropyl group, Ac stands for an acetyl group, TMS stands for a trimethylsilyl group, t-Bu stands for a tertiary-butyl group, and Ph stands for a phenyl group. Shown in the column of "Physical property value" is a melting point (C) or "NMR", which means $^1$H-NMR. $^1$H-NMR data are shown in Tables 15 to 17. "decomp." in the table means that the compound decomposed at the indicated temperature. The arrow represents a binding position.

[Chem. 4]

(1-A)

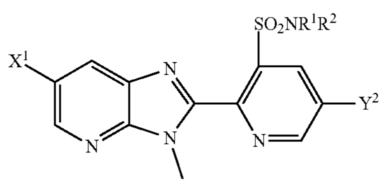

TABLE 1

| Compound No. | $R^1$ | $R^2$ | $X^1$ | $Y^2$ | Physical property value |
|---|---|---|---|---|---|
| 1-1 | Me | H | $CF_3$ | c-Pr | 154-156 |
| 1-2 | Et | H | $CF_3$ | c-Pr | 214-215 |
| 1-3 | Me | Me | $CF_3$ | c-Pr | 146-147 |
| 1-4 | $CH_2CH_2CH_2$ | | $CF_3$ | c-Pr | 98-100 |
| 1-5 | $CH_2CH_2CH_2CH_2$ | | $CF_3$ | c-Pr | 73-75 |
| 1-6 | Me | H | $CF_3$ | 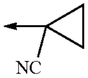 | 154-156 |
| 1-7 | Me | Me | $CF_3$ | 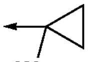 | 143-144 |
| 1-8 | Me | H | $CF_3$ | 4-FPh | 215-217 |
| 1-9 | Me | Me | $CF_3$ | 4-FPh | 215-217 |
| 1-10 | $CH_2CH_2CH_2$ | | $CF_3$ | 4-FPh | 89-91 |
| 1-11 | Me | H | $CF_3$ | 3-$CF_3$Ph | 169-170 |
| 1-12 | Me | Me | $CF_3$ | 3-$CF_3$Ph | 180-182 |
| 1-13 | $CH_2CH_2CH_2$ | | $CF_3$ | 3-$CF_3$Ph | 189-192 |
| 1-14 | Me | Me | $CF_3$ | $CO_2Me$ | 193-194 |
| 1-15 | Me | Me | $CF_3$ | CONHMe | 272-273 |
| 1-16 | Me | Me | $CF_3$ | $CONMe_2$ | 208-209 |
| 1-17 | Me | Me | $CF_3$ | Br | 175-177 |
| 1-18 | Me | H | $CF_3$ | Br | 104-105 |
| 1-19 | Me | Me | $CF_3$ | $NHCO_2$—t-Bu | 138-141 |
| 1-20 | Me | Me | $CF_3$ | N(Me)$CO_2$—t-Bu | NMR |

TABLE 2

| Compound No. | $R^1$ | $R^2$ | $X^1$ | $Y^2$ | Physical property value |
|---|---|---|---|---|---|
| 1-21 | Me | Me | $CF_3$ | $OCH_2CF_3$ | NMR |
| 1-22 | Me | Me | $CF_3$ | OMe | 145-147 |
| 1-23 | Me | H | $CF_3$ | OMe | 191-192 |
| 1-24 | Me | Me | $CF_3$ | $SO_2Et$ | 180-182 |
| 1-24 | Me | Me | $CF_3$ | SEt | 79-80 |
| 1-25 | Me | Me | $CF_3$ | $NHCH_2$—c-Pr | 120-122 |
| 1-26 | Me | Me | $CF_3$ | H | 155-157 |
| 1-27 | Me | Me | $CF_3$ | NHAc | 250(decomp.) |
| 1-28 | Me | Me | $CF_3$ | $NH_2$ | 114-116 |
| 1-29 | Me | Me | $CF_3$ | $NHCONMe_2$ | NMR |
| 1-30 | Me | Me | $CF_3$ | 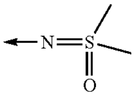 | 161-162 |
| 1-31 | Me | Me | $CF_3$ | 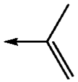 | NMR |
| 1-32 | Me | Me | $CF_3$ | $NHCH_2CH_2OMe$ | 89-90 |
| 1-33 | Me | Me | $CF_3$ | i-Pr | 121-122 |
| 1-34 | Me | Me | $CF_3$ | 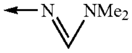 | 196-198 |
| 1-35 | Me | Me | $CF_3$ | 4-$OCF_3$—Ph | 174-176 |
| 1-36 | Me | Me | $CF_3$ | 3,4-$F_2$—Ph | 157-159 |
| 1-37 | Me | Me | $CF_3$ | 4-TMS—Ph | 217-219 |
| 1-38 | Me | Me | $CF_3$ | 3-CN—4-F—Ph | 236-238 |
| 1-39 | Me | Me | $CF_3$ | 3-SMe—Ph | 180-182 |
| 1-40 | Me | Me | $CF_3$ | 4-Ac—Ph | 197-198 |

TABLE 3

| Compound No. | $R^1$ | $R^2$ | $X^1$ | $Y^2$ | Physical property value |
|---|---|---|---|---|---|
| 1-41 | Me | Me | $CF_3$ | 4-CHO—Ph | 160-162 |
| 1-42 | Me | Me | $CF_3$ | 4-$CO_2Me$—Ph | 230-231 |
| 1-43 | Me | Me | $CF_3$ | 4-NHAc—Ph | 253-255 |
| 1-44 | Me | Me | $CF_3$ | 3,4,5-$F_3$—Ph | 170-172 |
| 1-45 | Me | Me | $CF_3$ | 3-Et—Ph | 164-166 |
| 1-46 | Me | Me | $CF_3$ | 3-OMe—Ph | 159-161 |
| 1-47 | Me | Me | $CF_3$ | 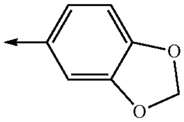 | 190-192 |
| 1-48 | Me | Me | $CF_3$ | 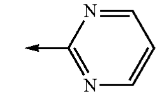 | NMR |
| 1-49 | Me | Me | $CF_3$ | 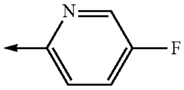 | NMR |
| 1-50 | Me | Me | $CF_3$ | 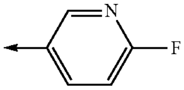 | NMR |
| 1-51 | Me | Me | $CF_3$ | 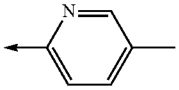 | NMR |

TABLE 3-continued

| Compound No. | $R^1$ | $R^2$ | $X^1$ | $Y^2$ | Physical property value |
|---|---|---|---|---|---|
| 1-52 | Me | Me | $CF_3$ | 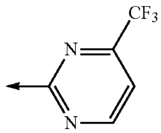 | NMR |
| 1-53 | Me | Me | $CF_3$ | 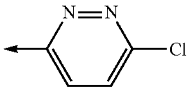 | NMR |
| 1-54 | Me | Me | $CF_3$ | 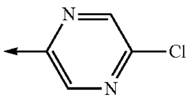 | NMR |

TABLE 4

| Compound No. | $R^1$ | $R^2$ | $X^1$ | $Y^2$ | Physical property value |
|---|---|---|---|---|---|
| 1-55 | Me | Me | $CF_3$ | 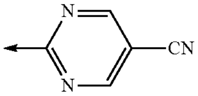 | NMR |
| 1-56 | Me | Me | $CF_3$ | 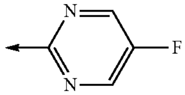 | NMR |
| 1-57 | Me | Me | $CF_3$ | 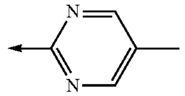 | NMR |
| 1-58 | Me | Me | $CF_3$ | 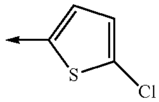 | NMR |
| 1-59 | Me | Me | $CF_3$ | 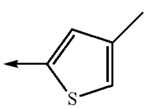 | NMR |
| 1-60 | Me | Me | $CF_3$ | 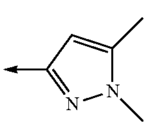 | NMR |
| 1-61 | Me | Me | $CF_3$ | 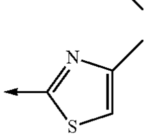 | NMR |
| 1-62 | Me | Me | $CF_3$ | 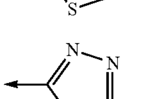 | NMR |
| 1-63 | Me | Me | $CF_3$ | 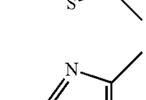 | NMR |

TABLE 4-continued

| Compound No. | $R^1$ | $R^2$ | $X^1$ | $Y^2$ | Physical property value |
|---|---|---|---|---|---|
| 1-64 | Me | Me | $CF_3$ | 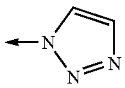 | NMR |
| 1-65 | Me | Me | $CF_3$ | 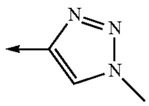 | NMR |

TABLE 5

| Compound No. | $R^1$ | $R^2$ | $X^1$ | $Y^2$ | Physical property value |
|---|---|---|---|---|---|
| 1-66 | Me | Me | $CF_3$ | 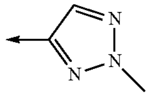 | NMR |
| 1-67 | Me | Me | $CF_3$ | 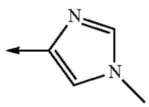 | NMR |
| 1-68 | Me | Me | $CF_3$ | 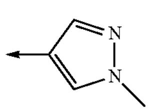 | NMR |
| 1-69 | Me | Me | $CF_3$ | 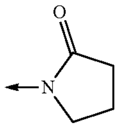 | NMR |
| 1-70 | Me | Me | $CF_3$ | 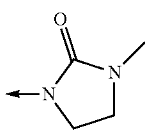 | NMR |
| 1-71 | Me | Me | $CF_3$ | 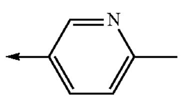 | NMR |
| 1-72 | Me | Me | $CF_3$ | 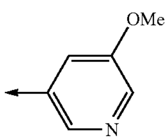 | NMR |
| 1-73 | Me | Me | $CF_3$ | 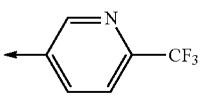 | NMR |
| 1-74 | Me | Me | $CF_3$ | 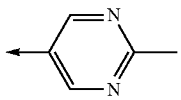 | NMR |

TABLE 5-continued

| Compound No. | $R^1$ | $R^2$ | $X^1$ | $Y^2$ | Physical property value |
|---|---|---|---|---|---|
| 1-75 | Me | Me | $CF_3$ | 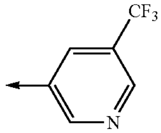 | NMR |

[Chem. 5]

(1-B)

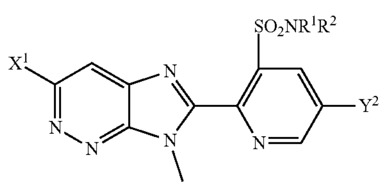

TABLE 6

| Compound No. | $R^1$ | $R^2$ | $X^1$ | $Y^2$ | Physical property value |
|---|---|---|---|---|---|
| 2-1 | Me | H | $CF_3$ | $CF_3$ | 196-197 |
| 2-2 | Me | Me | $CF_3$ | $CF_3$ | 178-179 |
| 2-3 | Me | Me | $CF_3$ | 4-FPh | 201-203 |
| 2-4 | Me | Me | $CF_3$ | 3-$CF_3$Ph | 243-245 |
| 2-5 | Me | H | $CF_2CF_3$ | 4-FPh | 249-251 |
| 2-6 | Me | Me | $CF_2CF_3$ | 4-FPh | 242-244 |
| 2-7 | $CH_2CH_2CH_2$ | | $CF_2CF_3$ | 4-FPh | 242-244 |
| 2-8 | Me | H | $CF_2CF_3$ | 3-$CF_3$Ph | 189-191 |
| 2-9 | Me | Me | $CF_2CF_3$ | 3-$CF_3$Ph | 228-230 |
| 2-10 | $CH_2CH_2CH_2$ | | $CF_2CF_3$ | 3-$CF_3$Ph | 209-211 |
| 2-11 | Me | Me | $CF_2CF_3$ | 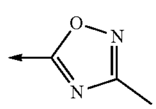 | 187-188 |
| 2-12 | Me | Me | $CF_2CF_3$ | 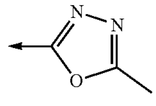 | 181-182 |
| 2-13 | Me | Me | $CF_2CF_3$ | $CO_2H$ | 129-130 |
| 2-14 | Me | Me | $CF_2CF_3$ | $CO_2Me$ | 176-177 |
| 2-15 | Me | Me | $CF_2CF_3$ | $CONMe_2$ | 176-177 |
| 2-16 | Me | Me | $CF_2CF_3$ | $NHCO_2$—t-Bu | 53-55 |
| 2-17 | Me | Me | $CF_2CF_3$ | I | 198-200 |

[Chem. 6]

(1-C)

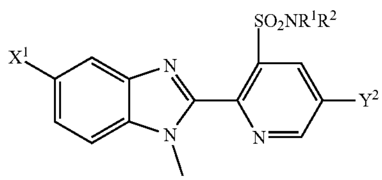

TABLE 7

| Compound No. | $R^1$ | $R^2$ | $X^1$ | $Y^2$ | Physical property value |
|---|---|---|---|---|---|
| 3-1 | Me | H | $OCF_3$ | H | 199-200 |
| 3-2 | Me | H | $OCF_3$ | H | 145-147 |
| 3-3 | Me | Me | $OCF_3$ | c-Pr | 90-92 |
| 3-4 | Me | H | $SO_2CF_3$ | 4-F—Ph | 240-241 |
| 3-5 | Me | Me | $SO_2CF_3$ | 4-F—Ph | 189-190 |

[Chem. 7]

(1-D)

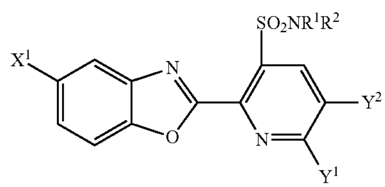

TABLE 8

| Compound No. | $R^1$ | $R^2$ | $X^1$ | $Y^1$ | $Y^2$ | Physical property value |
|---|---|---|---|---|---|---|
| 4-1 | Me | H | $SCF_3$ | H | H | 72-76 |
| 4-2 | Me | Me | $SCF_3$ | H | H | NMR |
| 4-3 | Me | H | $SCF_3$ | H | c-Pr | 149-150 |
| 4-4 | Me | H | $SOCF_3$ | H | c-Pr | 168-169 |
| 4-5 | Me | H | $SO_2CF_3$ | H | c-Pr | 199-200 |
| 4-6 | Me | Me | $SCF_3$ | H | c-Pr | 91-92 |
| 4-7 | Me | Me | $SOCF_3$ | H | c-Pr | 80-82 |
| 4-8 | Me | Me | $SO_2CF_3$ | H | c-Pr | 75-77 |
| 4-9 | Me | H | $SO_2CF_3$ | H | 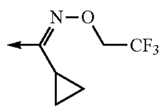 | 121-123 |
| 4-10 | Me | Me | $SO_2CF_3$ | H | 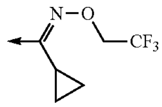 | 76-78 |
| 4-11 | Me | Me | $SO_2CF_3$ | | CHCHCClCH | 197-198 |
| 4-12 | Me | Me | $SCF_3$ | H | $CO_2Me$ | 120-122 |
| 4-13 | Me | Me | $SCF_3$ | H | $CO_2NHMe$ | 211-213 |
| 4-14 | Me | Me | $SCF_3$ | H | $CO_2NMe_2$ | 122-125 |
| 4-15 | Me | Me | $SCF_3$ | H | $CO_2NH$—c-Pr | 194-196 |
| 4-16 | Me | Me | $SCF_3$ | H | $CO_2NHCH_2CH_2OMe$ | 183-184 |
| 4-17 | Me | Me | $SOCF_3$ | H | 4-F—Ph | 175-177 |

[Chem. 8]

(1-E)

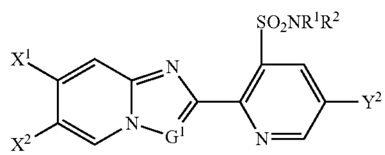

TABLE 9

| Compound No. | $R^1$ | $R^2$ | $X^1$ | $X^2$ | $Y^2$ | $G^1$ | Physical property value |
|---|---|---|---|---|---|---|---|
| 5-1 | Me | Me | $CF_3$ | H | 3-$CF_3$Ph | N | 169-171 |
| 5-2 | Me | H | $CF_3$ | H | 3-$CF_3$Ph | N | 201-203 |
| 5-3 | Me | Me | $CF_3$ | H | 3-$CF_3$Ph | N | 199-200 |
| 5-4 | Me | H | $CF_3$ | H | 4-FPh | N | 290-291 |
| 5-5 | Me | Me | $CF_3$ | H | 4-FPh | N | 184-186 |
| 5-6 | $CH_2CH_2CH_2$ | | $CF_3$ | H | 4-FPh | N | 214-216 |
| 5-7 | Me | H | H | $CF_3$ | 3-$CF_3$Ph | N | 195-197 |
| 5-8 | Me | Me | H | $CF_3$ | 3-$CF_3$Ph | N | 200-202 |
| 5-9 | Me | Me | H | $CF_3$ | Br | CH | 200-201 |
| 5-10 | Me | H | H | $CF_3$ | Br | N | 266-267 |
| 5-11 | Me | Me | H | $CF_3$ | Br | N | 152-153 |
| 5-12 | Me | Me | H | $CF_3$ | 4-F—Ph | CH | 203-204 |
| 5-13 | Me | Me | H | $CF_3$ | c-Pr | CH | 156-158 |
| 5-14 | Me | H | H | $CF_3$ | H | N | 110-112 |
| 5-15 | Me | H | H | $CF_3$ | c-Pr | N | 225-229 |
| 5-16 | Me | Me | H | $CF_3$ | c-Pr | N | 78-80 |
| 5-17 | Me | H | H | $CF_3$ | $NHCO_2$-t-Bu | N | 243-245 |
| 5-18 | Me | Me | H | $CF_3$ | $NHCO_2$-t-Bu | N | 203-205 |
| 5-19 | Me | Me | H | $CF_3$ | N(Me)$CO_2$-t-Bu | N | NMR |
| 5-20 | Me | Me | H | $CF_3$ | N($CH_2C{\equiv}CH$)$CO_2$-t-Bu | N | NMR |

[Chem. 9]

(1-F)

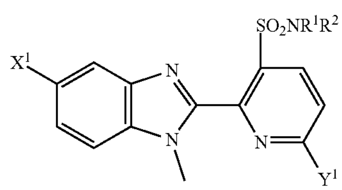

TABLE 10

| Compound No. | $R^1$ | $R^2$ | $X^1$ | $Y^1$ | Physical property value |
|---|---|---|---|---|---|
| 6-1 | Me | H | $SCF_3$ | 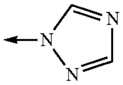 | NMR |
| 6-2 | Me | Me | $SCF_3$ | 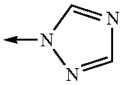 | NMR |

[Chem. 10]

(1-G)

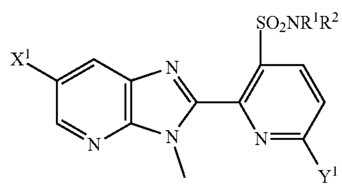

TABLE 11

| Compound No. | $R^1$ | $R^2$ | $X^1$ | $Y^1$ | Physical property value |
|---|---|---|---|---|---|
| 7-1 | Me | H | $CF_3$ | 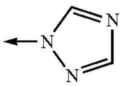 | 219-220 |
| 7-2 | Me | Me | $CF_3$ | 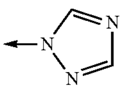 | 189-191 |
| 7-3 | $CH_2CH_2CH_2$ | | $CF_3$ | 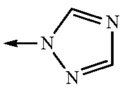 | 246-248 |

[Chem. 11]

(1-H)

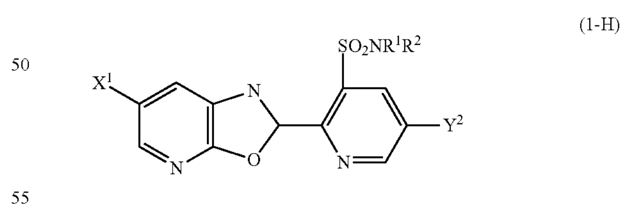

TABLE 12

| Compound No. | $R^1$ | $R^2$ | $X^1$ | $Y^2$ | Physical property value |
|---|---|---|---|---|---|
| 8-1 | Me | H | $CF_3$ | c-Pr | |
| 8-2 | Me | Me | $CF_3$ | c-Pr | |
| 8-3 | Me | H | $CF_3$ | 4-F—Ph | 301-303 |
| 8-4 | Me | Me | $CF_3$ | 4-F—Ph | 177-179 |

[Chem. 12]

(1-I)

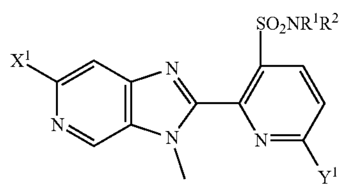

TABLE 13

| $R^1$ | $R^2$ | $X^1$ | $Y^1$ | Physical property value |
|---|---|---|---|---|
| Me | Me | $CF_3$ | Br | 240-241 |
| Me | Me | $CF_3$ | c-Pr | 241-242 |
| Me | Me | $CF_3$ | 4-F—Ph | 230-231 |
| Me | Me | $CF_3$ | 4-F—Ph | 217-219 |

[Chem. 13]

(1-J)

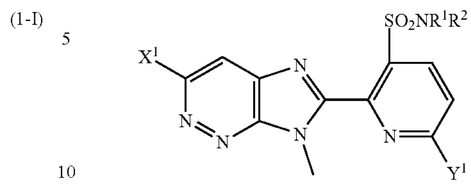

TABLE 14

| Compound No. | $R^1$ | $R^2$ | $X^1$ | $Y^1$ | Physical property value |
|---|---|---|---|---|---|
| 10-1 | Me | Me | $CF_2CF_3$ | i-Pr | |
| 10-2 | Me | Me | $CF_2CF_3$ | c-Pr | |
| 10-3 | Me | Me | $CF_2CF_3$ | 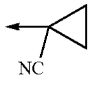 | |
| 10-4 | Me | Me | $CF_2CF_3$ | NHAc | |
| 10-5 | Me | Me | $CF_2CF_3$ | $NHCO_2Me$ | |
| 10-6 | Me | Me | $CF_2CF_3$ | $NHCONMe_2$ | |

TABLE 15

| Compound No. | $^1$H-NMR data ($CDCl_3$, $CD_3OD$, or DMSO-$d_6$) |
|---|---|
| 1-20 | 8.90(d, 1H), 8.74(dd, 1H), 8.38(d, 1H), 8.28(d, 1H), 3.76(s, 3H), 3.42(s, 3H), 2.82(s, 6H), 1.56(s, 9H) |
| 1-21 | 8.75(dd, 1H), 8.67(d, 1H), 8.28(d, 1H), 7.94(d, 1H), 4.52(q, 3H), 3.55(s, 3H), 2.78(s, 6H) |
| 1-29 | 8.98(d, 1H), 8.74(d, 1H), 8.38(d, 1H), 8.28(d, 1H), 5.68(s, 1H), 5.45(d, 1H), 3.76(s, 3H), 2.78(s, 6H), 2.29(s, 3H) |
| 1-31 | 8.98(d, 1H), 8.74(d, 1H), 8.38(d, 1H), 8.28(d, 1H), 5.68(s, 1H), 5.45(d, 1H), 3.76(s, 3H), 2.78(s, 6H), 2.29(s, 3H) |
| 1-48 | 9.49 (d, J = 2.1 Hz, 1H), 9.41 (s, 2H), 9.35 (s, 1H), 8.88 (s, 1H), 8.84 (d, J = 2.1 Hz, 1H), 8.65 (s, 1H), 3.69 (s, 3H), 2.82 (s, 6H) |
| 1-49 | 9.49 (d, J = 1.8 Hz, 1H), 9.00 (d, J = 1.8 Hz, 1H), 8.77 (s, 1H), 8.68 (d, J = 2.8 Hz, 1H), 8.31 (s, 1H), 7.96 (dd, J = 8.7, 4.0 Hz, 1H), 7.63 (td, J = 8.2, 2.8 Hz, 1H), 3.80 (s, 3H), 2.85 (s, 6H) |
| 1-50 | 9.31 (d, J = 2.1 Hz, 1H), 8.83 (d, J = 1.3 Hz, 1H), 8.76-8.70 (m, 2H), 8.50-8.43 (m, 2H), 7.35-7.29 (m, 1H), 3.78 (s, 3H), 2.82 (s, 6H) |
| 1-51 | 9.69 (s, 1H), 9.00 (s, 1H), 8.88 (s, 1H), 8.66 (br d, J = 14.3 Hz, 2H), 8.23-8.31 (m, 1H), 7.88 (br d, J = 8.1 Hz, 1H), 3.68 (s, 3H), 2.78 (s, 6H), 2.42 (s, 3H) |
| 1-52 | 9.86 (d, J = 2.0 Hz, 1H), 9.47 (d, J = 5.1 Hz, 1H), 9.19 (d, J = 2.0 Hz, 1H), 8.89 (s, 1H), 8.67 (d, J = 1.5 Hz, 1H), 8.22 (d, J = 5.1 Hz, 1H), 3.70 (s, 3H), 2.78 (s, 6H) |
| 1-53 | 9.74 (s, 1H), 9.08 (s, 1H), 8.89 (s, 1H), 8.73 (d, J = 9.0 Hz, 1H), 8.66 (s, 1H), 8.24 (d, J = 9.0 Hz, 1H), 3.70 (s, 3H), 2.80 (s, 6H) |
| 1-54 | 9.75 (d, J = 1.8 Hz, 1H), 9.49 (s, 1H), 9.05 (s, 1H), 9.03 (s, 1H), 8.89 (s. 1H), 8.66 (s, 1H), 3.69 (s, 3H), 2.79 (s, 6H) |
| 1-55 | 9.97 (d, J = 2.0 Hz, 1H), 9.44 (s, 1H), 9.19 (s, 2H), 8.79 (s, 1H), 8.32 (s, 1H), 3.83 (s, 3H), 2.88 (s, 6H) |

TABLE 16

| Compound No. | $^1$H-NMR data ($CDCl_3$, $CD_3OD$, or DMSO-$d_6$) |
|---|---|
| 1-56 | 9.82 (d, J = 1.7 Hz, 1H), 9.20 (s, 2H), 9.15 (d, J = 1.7 Hz, 1H), 8.88 (s, 1H), 8.65 (s, 1H), 3.69 (s, 3H), 2.78 (s, 6H) |
| 1-57 | 9.86 (d, J = 1.8 Hz, 1H), 9.19 (d, J = 1.8 Hz, 1H), 8.96 (s, 2H), 8.89 (s, 1H), 8.66 (s, 1H), 3.70 (s, 3H), 2.79 (s, 6H), 2.42 (s, 3H) |
| 1-58 | 9.31 (br s, 1H), 8.88 (br s, 1H), 8.64 (br s, 1H), 8.50 (br s, 1H), 7.96 (br s, 1H), 7.38 (br s, 1H), 3.68 (br s, 3H), 2.79 (br s, 6H) |

TABLE 16-continued

| Compound No. | $^1$H-NMR data ($CDCl_3$, $CD_3OD$, or DMSO-$d_6$) |
|---|---|
| 1-59 | 9.35 (d, J = 2.1 Hz, 1H), 8.93 (s, 1H), 8.69 (s, 1H), 8.53 (d, J = 2.1 Hz, 1H), 7.94 (s, 1H), 7.51 (s, 1H), 3.73 (s, 3H), 2.84 (s, 6H), 2.37 (s, 3H) |
| 1-60 | 9.26 (s, 1H), 8.75 (s, 1H), 8.69 (d, J = 2.0 Hz, 1H), 8.32 (s, 1H), 6.53 (s, 1H), 5.30 (s, 1H), 3.92-3.86 (m, 3H), 3.80-3.74 (m, 3H), 2.85-2.77 (m, 6H), 2.39-2.34 (m, 2H), 2.39-2.34 (m, 1H) |
| 1-61 | 9.43 (s, 1H), 8.89 (s, 1H), 8.77 (s, 1H), 8.31 (s, 1H), 7.14 (s, 1H), 3.80 (s, 3H), 2.85 (s, 6H), 2.60 (s, 3H) |
| 1-62 | 9.41 (s, 1H), 8.94 (s, 1H), 8.78 (s, 1H), 8.31 (s, 1H), 3.82 (s, 3H), 2.95 (s, 3H), 2.87 (s, 6H) |
| 1-63 | 9.43 (d, J = 1.9 Hz, 1H), 8.94 (d, J = 1.9 Hz, 1H), 8.79 (s, 1H), 8.33 (s. 1H), 3.82 (s, 3H), 2.87 (s, 6H), 2.83 (s, 3H) |
| 1-64 | 9.67 (d, J = 2.3 Hz, 1H), 9.27 (d, J = 1.2 Hz, 1H), 8.94-8.86 (m, 2H), 8.67 (s, 1H), 8.17 (d, J = 1.1 Hz, 1H), 3.70 (s, 1H), 2.82 (s, 6H). |
| 1-65 | 9.49 (d, J = 1.6 Hz, 1H), 9.02 (s, 1H), 8.87 (s, 1H), 8.78 (d, J = 1.7 Hz, 1H), 8.63 (s, 1H), 4.19 (s, 3H), 3.67 (s, 3H), 2.78 (s, 6H) |
| 1-66 | 9.31 (s, 1H), 8.81 (s, 1H), 8.76 (d, J = 1.8 Hz, 1H), 8.38 (s, 1H), 8.07 (s, 1H), 4.34 (s, 3H), 3.82 (s, 3H), 2.86 (s, 6H) |
| 1-67 | 9.45 (s, 1H), 9.23 (br s, 1H), 8.83-8.98 (m, 1H), 8.70 (s, 1H), 8.55 (br s, 1H), 8.26 (s, 1H), 7.50-7.65 (m, 1H), 3.66-4.04 (m, 6H), 2.77-2.91 (m, 6H) |

TABLE 17

| Compound No. | $^1$H-NMR data ($CDCl_3$, $CD_3OD$, or DMSO-$d_6$) |
|---|---|
| 1-68 | 9.30 (d, J = 2.1 Hz, 1H), 8.86 (d, J = 1.2 Hz, 1H), 8.65-8.58 (m, 2H), 8.50 (d, J = 2.1 Hz, 1H), 8.29 (s, 1H), 3.94 (s, 3H), 3.65 (s, 3H), 2.78 (S, 6H) |
| 1-69 | 9.13 (d, J = 2.4 Hz, 1H), 8.95 (d, J = 2.4 Hz, 1H), 8.85 (d, J = 1.5 Hz, 1H), 8.61 (d, J = 1.5 Hz, 1H), 4.05 (t, J = 7.1 Hz, 2H), 3.62 (s, 3H), 2.75 (s, 6H), 2.62 (t, J = 7.9 Hz, 2H), 2.17 (quin, J = 7.4 Hz, 2H) |
| 1-70 | 8.99 (d, J = 2.4 Hz, 1H), 8.91 (d, J = 2.6 Hz, 1H), 8.79 (s, 1H), 8.40 (d, J = 1.5 Hz, 1H), 4.14-3.99 (m, 2H), 3.72 (s, 3H), 3.69-3.62 (m, 2H), 2.94 (s, 3H), 2.79 (s, 6H) |
| 1-71 | 9.42 (d, J = 2.0 Hz, 1H), 9.04 (d, J = 2.1 Hz, 1H), 8.88 (d, J = 1.1 Hz, 1H), 8.66 (dd, J = 1.8, 9.3 Hz, 2H), 8.29 (dd, J = 2.4, 8.1 Hz, 1H), 7.49 (d, J = 8.1 Hz, 1H), 3.68 (s, 3H), 2.81 (s, 6H), 2.59 (s, 3H) |
| 1-72 | 9.16 (d, J = 1.5 Hz, 1H), 8.80 (d, J = 1.3 Hz, 1H), 8.63-8.57 (m, 2H), 8.51 (br d, J = 1.8 Hz, 1H), 8.33 (d, J = 1.7 Hz, 1H), 7.56 (s, 1H), 4.04 (s, 3H), 3.84 (s, 3H), 2.86 (s, 6H) |
| 1-73 | 9.51 (d, J = 2.0 Hz, 1H), 9.36 (d, J = 1.8 Hz, 1H), 8.89 (s, 1H), 8.82 (d, J = 2.0 Hz, 1H), 8.73-8.62 (m, 2H), 8.16 (d, J = 8.2 Hz, 1H), 3.70 (s, 3H), 2.82 (s, 6H) |
| 1-74 | 9.34 (d, J = 2.1 Hz, 1H), 9.20 (s, 2H), 8.85-8.77 (m, 2H), 8.45 (d, J = 1.5 Hz, 1H), 3.78 (s, 3H), 2.82 (s, 6H), 2.81 (s, 3H) |
| 1-75 | 9.36 (d, J = 1.5 Hz, 1H), 9.30 (s, 1H), 9.05 (s, 1H), 8.82 (d, J = 1.3 Hz, 2H), 8.67 (s, 1H), 8.44 (s, 1H), 3.77 (s, 3H), 2.82 (s, 6H) |
| 4-2 | 8.95(d, 1H), 8.39(dd, 1H), 8.16(d, 1H), 7.76-7.67(m, 3H), 2.88(s, 6H) |
| 5-19 | 8.85(d, 1H), 8.77(d, 1H), 8.35(d, 1H), 8.11(s, 1H), 7.28(dd, 1H), 3.41(s, 3H), 2.86(s, 6H), 1.53(s, 9H) |
| 5-20 | 8.95(d, 1H), 8.77(d, 1H), 8.39(d, 1H), 8.12(t, 1H), 7.28(dd, 1H), 4.54(d, 2H), 2.88(s, 6H), 2.35(t, 1H), 1.53(s, 9H) |
| 6-1 | 9.13(s, 1H), 8.71(d, 1H), 8.21(d, 1H), 8.20(s, 1H), 8.17(s, 1H), 7.52(d, 1H), 7.56(d, 1H), 4.00(s, 3H), 2.86(d, 3H) |
| 6-2 | 9.12(s, 1H), 8.59(d, 1H), 8.26(d, 1H), 8.16(s, 1H), 8.13(d, 1H), 770(dd, 1H), 7.51(d, 1H), 3.72(s, 3H), 2.76(s, 6H) |

The agricultural or horticultural insecticide comprising the condensed heterocyclic compound having a sulfonamide group represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, rnites and ticks. etc.

Specific examples of the pests, nematodes, etc. include the following: the species of the order Lepidoptera such as Parasa consocia, Anomis mesogona, Papillo xuthus, Matsumuraeses azukivora, *Ostrinia* scapula/is, *Spodoptera exempta, Hvphanria cunea, Ostrinia furnacalis, Pseudaletia separata, Tinea translucens*, Bactra jfirflrana, Parnara guttata M arasmia *exigua*, Parnara guttata, Sestamia inferens, Brachmia triannulela, MOnema lfavescens, *Trichoplusia* nti, Pleuroptya ruralis, Cystidia couaggaria, Lampides boeticus, Cephondes hylas, lelicoverpa *armigera*, Phalerodonta manieyi, Eumeta japoniea, *Pieris brassicae, Malacosoma neustria* testacea, stathmopoda mnasinissa, Cuphodes diospyrosella, *Archips* xylosteanus, *Agrotis segetum*, Tetramoera schislaceana, Papio machaon hippocrates, Endoclvta *sinensis, Lyonetia* prunilolieIla, Phylonor,Ycter ringoneella, *Cydia* kurokoi, Eucoenogenes aestuosa, *Lobesia botrana, Latoia sinica*, Euzophera batangensis, Phalonkdia mesoPpa, Spil/osoma impariis, Glyphodeas pyloahs, Olethreutes mori, ineola bisselliella, Endoclyta exerescens, Nemapogon granellus, Synanthedon hector, Cdia pomaonella, Plulella xylosvella, Cnaphalocrocis nedainalis, Sesamva calamistis, Scirpophag a incertulas, Pediasia *teterrellus*. *Phthorimaea* operculelia, Stauropus fagipersmidis, Etiella zinckenella, *Spodoptera exigua*, Palpifer sexnOtata, Spodaptera mautia, Scirpophaga innotata, Xestia c-n/gram, SpOptera *depravata*, Ephestia kuehniellia, Angerona prunaria, Clostera anastonosis, *Pseudoplusia includens*, latsunuraeses falcana, *Helicoverpa* assuila, *Autographa* nigrisigna, Agratis ipsilan. *Euproctis* pseudoconspersa, *Adoxophyes orana*, Caloptia theivora, Homona magnanima, Eplhestia elutella, Eumeta minuscula, Clostera anachoreta, Heliolhis *maritima*, Sparganathis piheriana, Busseola jisca, *Euproctis* sub/lava, Biston *robustum, Heliothis zea*, Aed/a leucomelas, Narosoideus jlavidorsalis, Viminia rumicis, *Bucculatrix* rpyrivore % la, *Grapholita molesta*, Soulerina astaurota, Ecto-Yelois pyrivorella, Cthilo *suppressalis, Acrolepiopsis* sapporensis, Pladia interpuncteiia, *Hellula* undais, *Sitotroga* cerealeila, Spadaptera *litura*, a species of the family Tofrricidae (Eucosma aparema), Acleris comariana, Scopelodes contractus, *Orgyia* thyellina, Spodaptera frugierda. *Ostrinia* zaguliaevi, Aaranga aenescens, Andraca birunctata, Paranthrene *regalis, Acosneryx castanea, Phylocnistis* toparcha, Endapiza *viteana, Eupoecillia ainbiguella, Anticarsia* genmatalis, Cnephasia cinereipalpana, Lymaniria *dispar*, Dendrolimus speclahilis, Leguminivora gltcinivtrella, Maruca testulalis, Mcatsumuraesesph aseoi, Caloptilia savella, *Phylocnistis* cilrelia, Omiodes indicata, *Archips* fiscacupreanaus, Acanthoplusia agnata, Bambalhna sp, Carposina niponensis, Conogethes puncqferalis, Synanthedon sp, Lyoneia *clerkella*, Papilio helenus, Colias erale poliographus, Phaleraflavescens, the species of the family Pieridae such as *Pieris rapae* crucivora and *Pieris rapae, Euproctis similis, Acrolepiopsis suzukiella, Ostrinia* nubiialis, *Mamestra brassicae*, Ascotis selenaria, Phtheochrokdes *clandestina*, Hoshinoa adAmbratana, Odonestis *pruni* japonensis, Triaena internmedia, *Adoxophyes orana* fisciata, Graplita *inopinata*, Spilonola ocellana, Spilonota lechriaspis, Illiheris *pruni, Argyresthia* conlugella, Caloptilia zachrvsa, *Archips* breviplicanus, Anomis *flava, Pectinophora gossypiella*, Aolarcha clerogata, *Diaphania* indica, *Heliothis virescens* and Earlas cupreoviridis;

the species of the order Hemiptera such as *Nezara antennata*, Stenous rubrovittatus, *Graphosoma* ruhrohineatum, Trigonotyus coelestialim, Aeschynteles naculatus, Creontiades pallidifer, Dvsdercus *cingulatus*, Chrysoniphaslscus, Aonldiella *aurantii, Graptopsaltria nigrofurscata, Blissus leucopterus, Icerya purchasi, Piezodorus* hybneri, Lagynotomus *elongatus*, ihaia subrulfi, Scatinophara *lurida, Sitobion* ibarae, Stariodes cwasakli, Aspidious deslructor, Tiylorilygus paicdulus, Alyzus muniecola, Psedaaulacaspis prnicola, Acyrthasiphon *pisum*, Anacanthocoris striicornis, Eciometapterus micantulus, *Eysarcoris lewisi*, Molpterxilfblginosa, Cicadella *viridis*, Rhopalosophum rufiahdominalis, Saissetia *oleae*, Trialeuroces vaporariorm, Aguriahana *quercus*, lvgus spp, Euceraphis pancltpennis, Andaspis kashicola, Coccus pseudcmagnolarumn, Cavelerius saccharivorus, Galeatus spinifrons, Macrosiphoniella sanborni, Aonidella citrina, lalyomorpiha nisla, Stephianitis jsciicarina, *Trioza* camphorae, Leptocorisa *chinensis*, Mioza quercicohai, Uhlerites latius, Ervthroneura comes, Paromius *exiguus*, Dupaspidiotus claviger, NVephiotettix *nigropictus, Halticiellus insularis, Perkinsiella saccharicida, Psyla* malivorella, Anomomeuramari, Pseudococcus longispinis, Pseudaulacaspis pentagona, *Pulvinaria* kuwacola, Apolygus *lucorum*, Togo *hemipterus*, foxoptera *aurantii*, Saccharicoccus *sacchari* Geoica luciluga, Numaa nuir, Comstockaspis perniciosia, Unaspis *citri, Aulacorthun solani, Eysarcoris ventralis*, Beniisia argentiiolii, Cicadella spectra, Aspidiotus hederae, iorhyssus hyalinus, Calopvha nigridorsalis, *Sogatella* jurcifera, *Megoura crassicauda, Brevicoryne brassicae, Aphis* glycines, Lepiocorisa oratorius, Nepholettix *virescens, Ufroeuconj ormnosianum, Cyrtopeltis tennuis, Bemisia tabaci, Lecaniun persicae*, Parlatoria theae, Pseudaonidia paeoniae, *Empoasca* onuaii, Pautia slali, *Dysaphis* tuipac, Macrosiphumin *euphorbiae*, Stephanitis pyrioides, (Ceroplases ceriferus, Parliatoria camehiae, Apohygus spinolai, *Nephotettix cincticeps*, Glaucias *subpunctatus*, Orthotylus flavosparsus, Rhopalosiphumn mais, *Peregrinus maidis, Eysarcoris parvus, Cimex*ectuarius, *Psyla* abieti, Nilaparivata ugens, *Psyla* tobrae, Eurydema *rugosum, Schizaphis piricola, Psyla pyricola*, Paratoreopsis pyri, Stephanitis nashi, Dysniicoccus wistfariae, Lepholeucaspis *japonica, Sappaphis piri, Lipaphis* erysimii, Neotoxoptera formnosana, Rhopalosophum nymphaeae. Eavardsiana *rosae*, Pinnaspis aspidistrue, *Psyla alni*, Speusoettix subjisculus, Alnetoidia aneli, *Sogatella* panicicola,Adelphocoris lineolatus, Dysdiercus poeciius, Parlatoria ziziphi, Uherites debile, *Laodelphax* strhatellus, Eurydemna pulchrumn, Cletus trigonus, Clovia *punctata*, Eipoasca spp, Coccus *hesperidum, Pachybrachius luridus*, Phanococcus kraunhiae, Stenotus binotatus, Arboridia *apicalis*, Macrosieles fascifrons, Dalycoris baccarum, Adelphocoris triannuilatus, *Viteus* vitifohli, Acanthocori sordidus, Leptocorisa *acuta*, Macropes obnublius, Cletus punchiger, Riptortus *clavatus*, Paratriosa cockerelli, Aphrophora costalis, *Lygus* dissponsi, *Lygus saundersi, Crisicoccus* pni, *Empoasca abietis, Crisicoccus mnatsumotoi, Aphis craccivora, Megacopta punctatissimumn, Eysarcoris* gutliger, Lepldosaphles beckhm, Diaphorina *citri, Toxoptera* citricidus *Planococcus citri, Duadeurodes citri*, Aeurocanthus spiniferus, Pseudococcus citriculus, Zyginella *citri, Pulvinaria citricola*, Coccus discrepans, Pseudaonidia duplex, Pulvnaria *aurantii*, Lecaniur corni, *Nezara viridula*, Stenodena calcaratum, Rhopalosiphun *padi, Sitobion* akebiae, Schizaplhis graminumn, Sorhoanus *tritici, Brachycaudus* hellchrysi, Carpocoris purpureipennis. *Myzus persicae*, Hfyalopterus *pruni, Aphis* farinose yanagicola, Measalis *populi*, Unaspis yanonensis, Mlesohomotonma carmphorae, *Aphis* spnraecola, *Aphis* pomni, Lepidosaphes umi, *Psyla mali*, Ieterocordyrlus fiaripes, tvzus mnalisuctus, Aphidonuguis *mali*, Orienus ishidai, *Ovatus* malicolens. Eriosoma lanigerun, Ceronplastes *rubens* and *Aphis* gossnpil;

the species of the order Coleoptera such as Xystrocera *globosa*, Paederus fiscipes, Eucetonia roelofi, Callosobruchus *chinensis*, Cylas fbrmicarius, IItpera poslica Echinocnenus squameus, Oulenaa or yzae, Donaciaprovosli, *Lissorhoptrus oryzophilus*, Colasposoma dauricun, Euscepespostiasciatus, *Epilachna varivestis*, AcanthosceAides oblectus, *Diabrotica* virgiera virgierra, Jnvolvlus cupreus, Aulaco Phorafenoralis, *Bruchus* pisorumi, *Epilachna* viginlioctomiaculata, C arpoprhilus dinidialus, *Cassida nebulosa*, Luperomorpha tunebrosa, Phyliotreta *striolata, Psacothea hilaris*, Aeolesthes chrysothrix, Curculio *sikkimensis*, Carpophilus heinpterus, Oxycetoniia jcunda, *Diabrotica* spp, Aimeia *splendens*, Sitophius zeamais, bolium castaneurn, *Sitophilus oryzae*, Palorus subdepressus, *Melolontha japonica, Anoplophora* malastiaca, Neatus picipes, Lepthnotarsa decenlineata, *Diabrotica* undecim*punctata* howardi, Sphenophorus venatus, *Crioceris* quatuordecimpunclata, Conotrachelus nenuphar, Ceuthorhynchidius albosuluralis, *Phaedon brassicae*, Lasioderma serricorne, Silona japwonicus, Adoretuss tenuinaculatus, kenebrio *molitor*, Basilepta balyi, Hypera nigrirostris, *Chaetocnema* conlcinna, *Anomala cuprea*, Heplophyla i *picea*, E piachna vigintioctopunctola, *Diabrotica longicornis, Eucelonia pilifera Agriotes* spp, Atlagenus unicolor *japonicus, Pagria signata*, Anonala rufocuprea, Palorus ratzeburgii, Alphitobius kaevigatus, Anthrenus *verbasci, Lycius brunneus*, Tiboliunm confuisun, MeAethia nigrobilineata, Xylotrechus pyrrhoderus, *Epitrix* cucuneris, ibmiicuspinipercd, afonochnamus alternoaus, Poillia jalponica, Epicauto gorhani, *Sitophilus* zeamais, Rhynchites *heros*, Listroderes costirostris, Callosobruchus *maculatus*, Phylobrus arnaus, Anthonomnus pomorun, Linacidea aenea and *Anthonomus grandis;* the species of the order Diptera such as *Culex pipiens pallens, Pegoya hyoscyani, Liriomyza huidobrensis, Musca* domeslico, Chllorops *oryzae*, Hydrellia sasakii, Agromyza *oryzae*, Hydrellia griseola, Hydrellia griscola, Ophioryia *phaseoli*, Docus cucurbitae, Drosophla suzukii, Rhacochlaena *japonica, Muscina* stabuilans, the species of the farnily Phoridae such asMegaselia spiracularis, Clogmia albipunctala, DTpula aino, Phornita regina, *Culex* trilaeniorhynchus, Anopheles *sinensis*, lilenva *brassicae*, Asohondylia sp *Delia* piatura, *Delia* antiaua. Rhaolelis *cerasi*, Culexpiplens molestus Forskal, *Ceratitis capitata, Bradysia agrestis*, Pegamya cunicularia, Lriomyza *sativae, Liriomyza* bryoniae, CIromatomyia *horticola*, iriomyza *chinensis, Culex cuinquefjsciatus, Aedes aegvpti, Aedes* atbopictus, Liriolmyza trlfoli, *Liriomyza sativae, Dacus dorsalis, Dacus* tsuneonis, Sitodilosis moselana, Merormuza nigriventris, Anastrephaludens and *Rhagoletis pomonella;* the species of the order Hymenoptera such as Pristomyrmex *pungens*, Bethylid wasps, Mononorium *pharaonis, Pheidole noda, Athalia rosae*, Dryocosmus kuriphilus, Formica *fusca japonica*, Vespid wasps, Athaia injamaia infunata, Arge pagana, *Athalia japonica*, Acroinyrnex spp, Sotenopsis spp, Argenai and Ochetellus glaber;

the species of the order Orthoptera such as Romorocoryphus lineosus, *Grylotalpa* sp, *Oxya hylaintricata, Oxya yezoensis, Lucusta migratoria*, Oxyajoponica, H-omorocuryphus jezoensis and Teleogrylus emma;

the species of the order Thysanoptera such as Selenothrips rubrocinctus, Stenchaetothrips *biformis, Haplothrips aculeatus, Ponticulaothrips diospyrusi, Thrips flavus, Anaphothrips obscurus, Liothrips floridensis*, fhrips simplex, *Thrips nigropilosus, Heliothrips* haemorrhoidals, Pseudodendrothrips mori, Microcephaotihrips abdommlal/s, Leeuwemna pasani, Litoletothrips pasaniae, *Scirtothrips citri*, Haplo/hrips *chinensis, Mfycterothrips glycines, Thrips setosus, Scirtothrips dorsalis*, Dendrothrips minowai, Ha.plothrips *niger, Thrips tabaci*, hrips alliorun, *Thrips* hawai/ensis, IIaplotrips kurdumiovi, Cairothrips ianicatus, *Frankliniella intonsa*, Thrip?s *coloratus, Franklinella occidentalis, Thrips palmi* brankliniella lilivora and *Liothrips* vaneeckei;

the species of the order Acari such as Leptotrombidium akamushi, *Tetranychus* ludeni, *Dermacentor variabilis, Teiranvchus trunciatus, Ornithonyssus bacoti, Demodlex canis*, trranychus viennensis, *Tetranychus kanzawai*, the species of the family Ixodidae such as *Rhipicephalus* sangineus, Cheyletus *malaccensis*, Tvrophagus putrescentiae, Derinatophagoides fairinae, *Latrodectus* hasseltii, Dermacentur taiwvanensis, Acaphyla theavagrans, Poal,hagotarsonemus *latus*, Aculoos lyconersici. Ornithonvssus svlvairum, ktranvchus *urticae, Eriophves chibaensis, Sarcoptes scabiei, Haniemaphysalis iongicornis, Ixodes scapularis*, yrophagus simidis, Cheyletus erudiNus, Panunychus *citri, Cheylelus moorei, Brevipalpus phoenicis*, Octodectes cynois, Dermatophagoides ptrenvssnus, *Haemaphysalis* Ziava, *Ixodes ovatus, Phvlocoptruta citri, Aculus schlechtendali, Panonychus ulmi, Amblyomma americanum, Dermanyssus* galinae, Rhvzoglyphus robini and Sancassania sp.;

the species of the order Isoptera such as Reticuliternies niyatakei, Incisiternmes minor, Coptoterines *formosanus*, lodoiermopsis *japonica*, Reticuiterrnes sp, *Reticulitermes* iaviceps nanianus, Glypttermes kaushimensis, Copitoernes guangzhoensis, Neotermes koshunensis, Gotermes kodamai, Glyptoermes satsumensis, Cryptotermes *domesticus*, Odontotermes;fornosanus, Gvptotermes nakajimaL Pericaprilermes nitobei and Reliculilermes *speratus;* the species of the order Blattodea such as *Periplaneta*, fldiginosa, Battelia *germanica*, Blata orientahs, *Periplaneta brunnea*, Blarella htiuricolis, *Periplaneta japonica* and Periplanela americana;

the species of the order Siphonaptera such as *Pulex irritans, Ctenocephalides* felis and Ceratophyllus *gallinae;* the species of the phylum Nematoda such as Nothotylenchus *acris, Aphelenchoides besseyi, Pratylenchus penetrans, Meloidogyne hapla, Meloidogyne incognita, Globodera* rosochienasis, Meoidogyne *javanica*, leterodera glychnes, *Pratylenchus coffeae, Pratylenchus neglectus* and Tvlenchus *semipenetrans*; and the species of the phylum Moliusca such as *Pomacea* canaliculaa, Acharinafulica, Meghimatium bilineatum, Lehmannina valen/iana, Limax *flavus* and Acusadespeca *sieboldiana.*

In addition, the agricultural or horticultural insecticide of the present invention has a strong insecticidal effect on Tuta absoluta as well.

Further, animal-parasitic mites and ticks are also included in the target pests, and examples include the species of the family Ixodidae such as *Boophilus* miicroplus, *Rhipicephalus sanguineus, Haemaphysalis* Iongicornis, Haenaphysalisflava, Haenaphysalis canpanulata, Haenalphysalis *concinna, Haewhaphysals japonica*, Hlaenaphysalis kitokai, aenaphyvsalis las, *Ixodes ovatus, Ixodes nipponensis, Ixodes* persuicatus, Amblyonna testudinarliwn, Haemnaphysalis megaspinosa, Dermnacentor *reticulatus* and *Dermacentor taiwanensis*; Dernanyssus *gallinae*; the species of the genus *Ornithonyssus* such as *Ornithonyssus* syviarun and *Ornithonyssus* bursa; the species of the family Trombiculidae such as Eutronbicula wichmianni, Lejtotrombiduum akarushi, Leplotrombidliupalidun, Leptotrombidiumn fii, Leptotronmbidim nosa, Neotronibicula *autumnalis*, Eutronbicula alpheddugesi and Helenicula niyagawai; the species of the farily Cheyletidae such as *Cheyletiella* vasguri, Chevletiella *parasitivorax* and Chetletiella *blakei*; the species of the superfamily Sarcoptoidea such as *Psoroptes cuniculi, Chorioptes bovis, Otodectes cynoris, Sarcoptes scabiei* and Notoedres cati; and the species of the family Demodicidae such as Denodex *canis.*

Other target pests include fleas including ectoparasitic wingless insects belonging to the order Siphonaptera, more specifically, the species belonging to the families Pulicidae and Ceratophylidae. Examples of the species belonging to the family Pulicidae include *Ctenocephalides canis, Ctenocephalides felis, Pulex irritans, Echidnophaga gallinacea, Xenopsyla cheopis*. Leptopsyla segnis, *Nosopsylus* frasciatus and Alonopsylus *anisus.*

Other target pests include ectoparasites, for example, the species of the suborder Anoplura such as Haeniatopinus *eurysternus*, Haenatopinus asini, Dalnalinia *ovis, Linognathus vituli*, Haenmatoplnus suis, Phthirus pubis and *Pediculus* capitis; the species of the suborder Mallophaga such as *Trichodectes canis*; and hematophagous Dipteran insect pests such as Ibanus trigonus, Ciulicoides *schultzei* and Snimuliurn ornaurn. Also included are endoparasites, for example, nematodes such as lungworms, whip,worms, nodular worins, endogastric parasitic worms, ascarides and filarial worms; cestodes such as Spirormetra erinacei, Diphvlobothriun iatu, Dipidium caninun, *Multiceps* rnulticeps, *Echinococcus granulosus* and Lchinococcus mrultilocularis; trematodes such as Schistosamai ponicum andTFasciola *hepatica*; and protozoa such as coccidia, Plasnodiui, intestinal *Sarcocystis*, Toxoplasia and Cr,ypltsporidiun.

Specific Examples of the endoparasite include the following endoparasites: from the order Enoplida, for example, *Trichuris* spp, (whipworms), Capillaria spp. (hairworms), Trichonosoides spp, Richinella spp, (roundworms), etc.; from the order Rhabditida, for example, Micranena spp, Strongy/Oides spp, etc.; from the order Strongylida, for example, StrongyTus spp, (strongyles), Triodontophorus spp, Oesophagodontus spp, Trichonena spp, Gynaocephalus spp, Cylindropharynx spp, Poleriostomum spp, Cyclococercus spp, Cylicostephanus spp, Oesophagostanum spp, (nodule worms), *Chabertia* spp, Stephanurus spp. (Stephanurus dentalus), Ancytostoma spp, (Ancylostonia duadenale), UIncinaria spp, Bunastanun spp, Globocephaus spp, Synganius spp, Cyalhostmrna spp, 51 Metastrongylus spp, (iungworms), DicivocauIus spp, Muellerius spp, Protostrongylus spp, Neostrongylus spp, Cystocaulus spp, Pneunostrongvlus spp, Spicocaulus spp, Elahosirongylus spp, Parelaphostrongylus spp, Crenosana spp, Paracrenosoma spp, *Angiostrongylus* spp, (=Angiostrongyhus cantanensis), Aelurastrangylus spp, Filaroides spp, Parajilaroides spp, Tichostran$_g$ylus spp, (trichostrongyles), *Haemonchus* spp, (Haenianchus contartus), *Ostertagia* spp, Marshallagia spp, *Cooperia* spp, Nenatoirus spp, (nematodes), Hostrongylus spp, Obeliscoides spp, Aniidastanun spp, Ollulanus spp, etc.;

from the order Oxyurida, for example, Oxyuris spp, (Oxyuris equi), *Enterobius* spp. (pinworms), *Passalurus* spp, *Syphacia* spp, Aspiculuris spp, HeteraMcis spp, etc.;

from the orderAscaridia, for example, *Ascaris* spp, (ascarids), Taxascaris spp, Toxacara spp, (*Toxocara canis*), *Parascaris* spp, (*Parascaris equorum*), *Anisakis* spp, *Ascaridia* spp, etc.;

from the order Spirurida, for example, Gnathostoina spp, Physalaptera spp, *Thelazia* spp, Gangylanemaia spp, Habranemaia spp, Parabronenma spp, Draschia spp, iDracunculus spp, (*Dracunculus* nedinensis), etc;

from the order Filariida, for exanrple, Stephanotularna spp, Parafilaria spp, *Setaria* spp, *Loa* spp, *Dirofilaria* spp, (Dirojilaria imnitis), Litomosoides spp, *Brugia* spp, WIuchereria spp, *Onchocerca* spp, etc.; and from the order Gigantorhynchida, for example, Filiollis spp, *Moniliformis* spp, Macracanthorhynchus spp, Prosthenorchis spp, etc.

The endoparasite control agent comprising the condensed heterocyclic compound having a sulfonamide group represented by the general formula (1) of the present invention or a salt thereof as an active ingredient is effective against not only parasites that live in the body of an intermediate or final host, but also parasites that live in the body of a reservoir host. The condensed heterocyclic compound having a sulfonamide group represented by the general formula (1) of the present invention or a salt thereof is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage: sporozoites; etc. In the case of nematodes, the compound is effective against their eggs, larvae and adults. The compound of the present invention is capable of not only combating parasites in the living body, but also even preventing parasitic infection by application to the environment as a route of infection. For example, it can prevent the occurrence of soil-bome infection, i.e, infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites and ticks, fleas, lice, assassin bugs, trornbiculid mites, etc.; and the like.

For the control of ectoparasites or endoparasites in domestic mammals and birds using the compound of the present invention, an effective amount of the compound of the present invention with pharmaceutical excipiernts can be delivered by oral administration; parenteral administration such as injection (intramuscular, subcutaneous, intravenous, intraperitoneal); transdennal administration such as dipping, spraying, bathing, washing, pouring-on, spotting-on, or dusting; or transnasal administration. For the administration of the compound of the present invention, molded products containing the compound, such as strips, plates, bands, collars, earmarks. limb bands, and label devices, can also be used. The compound of the present invention can be formulated into any dosage form suitable for the administration route selected as appropriate.

Examples of the dosage form include solid preparations, such as powders, granules, wettable powders, pellets, tablets, bolus, capsules, and molded products containing the active compound; injectable solutions, oral solutions, and solutions for use on the skin or in body cavities; solution preparations, such as pour-on solutions. spot-on solutions, flowables, and emulsions; and semi-solid preparations such as ointments and gels. The solid preparations can be used mainly for oral administration or for transdermal administration after dilution with water, or for environmental treatment. The solid preparations can be produced by mixing the active compound, and if necessary an adjuvant, with an appropriate filler and then shaping the mixture into a desired form. Examples of the appropriate filler include inorganic substances such as carbonate salts, hydrogen carbonate salts, phosphate salts, aluminum oxide, silica, and clay; and organic substances such as sugar, cellulose, ground cereals, and starch.

The injectable solutions can be administered intravenously, intramuscularly, or subcutaneously. The injectable solutions can be produced by dissolving the active compound in an appropriate solvent, and if necessary, adding excipients such as solubilizing agents, acids, bases, buffer salts, antioxidants, and protecting agents to the solution. Examples of the appropriate solvent include water, ethanol, butanol, benzyl alcohol, glycerin, propylene glycol, polyethylene glycol, N-methyl pyrrolidone, and a mixture thereof, physiologically acceptable vegetable oils, and synthetic oils suitable for injection. Examples of the solubilizing agent include polyvinyl pyrrolidone, polyoxyethylated castor oil, and polyoxyethylated sorbitan ester. Examples of the protecting agent include benzyl alcohol, trichlorobutanol, p-hydroxybenzoic acid ester, and n-butanol Other additives commonly used in this field can be used as appropriate.

The oral solutions can be administered directly or after dilution. The oral solutions can be prepared as described above for the injectable solutions.

The flowables, emulsions, and the like can be used, directly or after diluted, for transdermal administration or for environmental treatment.

The solutions for use on the skin can be administered by pouring on, spreading, rubbing in, spraying, dispersing or dipping (dipping, bathing, or washing) or otherwise applying. These solutions can be prepared as described above for the injectable solutions.

The pour-on solutions and spot-on solutions are dripped or sprayed onto a defined area of the skin, and thereby the active compound is allowed to permeate through the skin and act systemically. The pour-on solutions and spot-on solutions can be prepared by dissolving, suspending, or emulsifying the active ingredient in an appropriate solvent or mixed solvent suitable for use on the skin. If necessary, an adjuvant such as a surfactant, a colorant, an absorption enhancer, an antioxidant, a light stabilizer, and/or an adhesive may be contained. Examples of the solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, N,N-dimethylformamide (DMF), liquid paraffin, light liquid paraffin, silicone, dimethylacetamide, N-methyl pyrrolidone, and 2,2-dimethyl-4-oxy-methylene-1,3-dioxolane. Examples of the absorption enhancer include dimethyl sulfoxide (DMSO), isopropyl myristate, dipropylene glycol pelargonate, silicone oil, aliphatic ester, triglyceride, and fatty alcohol. Examples of the antioxidant include sulfite salts, metabisulfite salts, ascorbic acid, butylated hydroxytoluene, butylated hydroxyanisole, and tocopherol. Other additives commonly used in this field can be used as appropriate.

The emulsions can be delivered by oral administration, transdermal administration, or injection. The emulsions can be prepared by dissolving the active ingredient in a hydrophobic or hydrophiilic phase and homogenizing a mixture of this solution and the other phase solvent with the addition of an appropriate emulsifier and if necessary an adjuvant such as a colorant, an absorption enhancer, a protecting agent, an antioxidant a light-shielding agent, and/or a thickener. This method is well established and may be employed in the present invention, Examples of the hydrophobic phase (oil) include paraffin oil, silicone oil, sesame oil, almond oil, castor oil: synthetic triglycerides; esters such as ethyl stearate, di-n-butyryl adipate, hexyl laurate, dipropylene glycol pelargonate, esters of branched short-chain fatty acids and saturated fatty acids of $C_{16}$-$C_{18}$ chain length, isopropyl myristate, isopropyl palmitate, caprylic or capric acid esters of saturated fatty alcohols of $C_{12}$-$C_{18}$ chain length, isopropyl stearate, oleyl oleate, decyl oleate, ethyl oleate, ethyl lactate, waxy fatty acid ester, dibutyl phthalate, and diisopropyl adipate; and alcohols such as isotridecyl alcohol, 2-octyldodecanol, cetyl stearyl alcohol, and oleyl alcohol.

Examples of the hydrophilic phase include water, propylene glycol, glycerin, and sorbitol.

Examples of the emulsifier include nonionic surfactants such as polyoxyethylated castor oil, polyoxyethylated sorbitan monoolefinate, sorbitan monostearate, glyceryl monostearate, polyoxyethyl stearate, and alkylphenol polyglycol ether; amphoteric surfactants such as disodium N-lauryl β-iminodipropionate and lecithin; anionic surfactants such as sodium lauryl sulfate, fatty alcohol ether sulfate, and monoethanolamine salts of mono-/di-alkyl polyglycol orthophosphoric acid ester; and cationic surfactants such as cetyltrimethylammonium chloride.

Other adjuvants include carboxymethyl cellulose, methyl cellulose, polyacrylate, alginate, gelatin, gum arabic, polyvinyl pyrrolidone, polyvinyl alcohol, methyl vinyl ether, maleic anhydride copolymers, polyethylene glycol, waxes, and colloidal silica.

The semi-solid preparations can be administered by applying or spreading them on the skin or introducing them into body cavities. The gels can be prepared by preparing a solution as described above for the injectable solutions and adding, to the solution, a. thickener in an amount sufficient to give a clear, ointment-like, viscous substance.

In the case where the endoparasite control agent of the present invention is used as a pharmaceutical for humans or non-human animals (e.g, non-human mammalian or avian species), the optimum amount (effective amount) of the active ingredient vanes with the purpose (treatment or prevention), the kind of infectious parasite, the type and severity of infection, the dosage form, etc. but in general, the oral daily dose is in the range of about 0.0001 to 10000 mg/kg body weight and the parenteral daily dose is in the range of about 0.0001 to 10000 mg/kg body weight. Such a dose may be given as a single dose or in divided doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that needs to be diluted to a suitable concentration before use.

The endoparasite control agent of the present invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural or horticultural insecticide comprising the condensed heterocyclic compound having a sulfonamide group represented by the general formula (1) of the present invention or a salt thereof as an active ingredient has a remarkable control effect on the above-described pests which damage lowland crops, field crops, fruit trees, vegetables, other crops, omamental flowering plants, etc. The desired effect can be obtained when the agricultural or horticultural insecticide is applied to nursery facilities for seedlings, paddy fields, fields, fruit trees, vegetables, other crops, ornamental flowering plants, etc. and their seeds, paddy water, foliage, growing media such as soil, or the like at an appropriate time depending on the expected time of pest infestation, i.e.. before pest infestation or upon the confirmation of pest infestation. In particular. systemic application is preferable. That is, the agricultural or horticultural insecticide is applied to nursery soil, soil in transplanting holes, plant foot, irrigation water, cultivation water in hydroponics, or the like so that the compound of the present invention is systemically absorbed into crops, ornamental flowering plants, etc. through the roots via soil or otherwise.

The useful plant to which the agricultural or horticultural insecticide of the present invention can be applied is not particularly limited. Examples of the useful plant include cereals (e.g, rice, barley, % heat, rye, oats, com, etc.), legumes (e.g, soybeans, azuki beans, broad beans, green peas, kidney beans, peanuts, etc.), fruit trees and fruits (e.g, apples, citrus fruits, pears, grapes, peaches, plums, cherries, walnuts, chestnuts, almonds, bananas, etc.), leaf and fruit vegetables (e.g, cabbages, tomatoes, spinach, broccoli, lettuce, onions, green onions (chives, Welsh onions, etc.), green peppers, eggplants, strawberries, pepper crops, okra, Chinese chives, etc.), root vegetables (e.g, carrots, potatoes, sweet potatoes, taros, Japanese radishes, turnips, lotus roots, burdock roots, garlic, Chinese scallions, etc.), crops for processing (e.g, cotton, hemp, beet. hops, sugarcane, sugar beet, olives, rubber, coffee, tobacco, tea, etc.), gourds (e.g.. Japanese pumpkins, cucumbers, watermelons, oriental sweet melons, melons, etc.), pasture grass (e.g, orchardgrass, sorghun, timothy, clover, alfalfa, etc.), lawn grass (e.g, Korean lawn grass, bent grass, etc.), spice and aromatic crops and ornamental crops (e.g, lavender, rosemary, thyme, parsley, pepper, ginger, etc.), ornamental flowering plants (e.g, *chrysanthemum*, rose, carnation, orchid, tulip, lily, etc.), garden trees (e.g. ginkgo trees, cherry trees, Japanese *aucuba*, etc.) and forest trees (e.g, A bies schainensis, *Picea* jezoensis, pine, yellow cedar, Japanese cedar, hinoki cypress, *eucalyptus*, etc.).

The "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydin; or other herbicides, such as bromoxynil, dicamba and 2.4-D.

Examples of the plant provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like. Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural or horticultural insecticide of the present invention can be applied to these plants as well Further, exemplary toxins expressed in genetically modified plants include insecticidal proteins of Bacilus *cereus* or *Bacillus* popilliae; *Bacillus thuringiensis* δ-endotoxins, such as Cry1Ab, Cry1Ac, Cry1F, Cry IFa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosone inactivating proteins (RIP), such as ricin, maize RIP, abrin, luffin, saporin and bryodin; steroid metabolizing enzymes, such as 3-hydroxy steroid oxidase, ecdvsteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP0374753A, WO93/07278, WO95/34656, EP0427529A, EP451878A, WO03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural or horticultural insecticide of the present invention can be used in combination or used systematically.

When the agricultural or horticultural insecticide of the present invention is used to control target insect pests or nematodes, it may or may not be diluted or suspended in water etc. and its effective amount for pest or nematode control is applied to plants potentially infested with the target insect pests or nematodes. For example, in order to control insect pests or nematodes that may damage crops such as fruit trees, cereals and vegetables, foliar application may be performed, and also seed treatment, such as dipping, dust coating, and calcium peroxide coating of seeds, may be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, rice nursery box treatment, and submerged application. In addition, application to growing media in hydroponics, smoking treatment, trunk injection, and the like can also be performed.

Further, the agricultural or horticultural insecticide of the present invention, with or without dilution or suspension in water etc. can be applied to sites potentially infested with pests in an amount effective for the control of the pests. For example, spray treatment of stored grain pests, house pests, sanitary pests, forest pests, etc. can be performed, and also coating, smoking, or baiting treatment of residential building materials can be performed.

Exemplary methods of seed treatment include dipping of seeds in a diluted or undiluted fluid of a liquid or solid formulation for the permeation of agrochemicals into the seeds: mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the seed treatment refers to a plant body which is in the early stages of cultivation and used for plant propagation. The examples include, in addition to what is called a seed, a plant body for vegetative propagation, such as a bulb, a tuber, a seed potato, a bulbil, a propagule, a discoid stem, and a stem used for cuttage.

The term "soil" or "growing medium" in the method of the present invention for using an agricultural or horticultural insecticide refers to a support medium for crop cultivation, in particular, a support medium which allows crop plants to spread their roots therein, and the materials are not particularly limited as long as they allow plants to grow. Examples of the support medium include what is called soil, seedling mats, and water, and specific examples of the materials include sand, pumice, vermiculite, diatomite, agar, gelatinous substances, high-molecular-weight substances, rock wool, glass wool, wood chip, and bark.

Exemplary methods of the application to crop foliage or to stored grain pests, house pests, sanitary pests, forest pests, etc. include application of liquid formulations such as emulsifiable concentrates or flowables, or solid formulations such as wettable powders or water-dispersible granules after appropriate dilution in water. Also included are dust application and smoking.

Exemplary methods of soil application include application of a water-diluted or undiluted liquid formulation to the foot of plants, nursery beds for seedlings, or the like; application of granules to the foot of plants, nursery beds for seedlings, or the like; application of dusts, wettable powders, water-dispersible granules, granules, or the like onto soil and subsequent incorporation of the formulation into the whole soil before seeding or transplanting; and application of dusts, wettable powders, water-dispersible granules, granules, or the like to planting holes, planting rows, or the like before seeding or planting.

In the case of the application to nursery boxes for paddy rice, dusts, water-dispersible granules, granules, or the like are used depending on whether the application is performed at the time of seeding, in the greening period, at the time of transplanting, or the like. Such formulations can be applied by incorporation into nursery soil. For example, dusts, water-dispersible granules, granules, or the like may be incorporated into bed soil, covering soil, or the whole nursery soil. Simply, nursery soil and such formulations may be alternately layered.

In the application to paddy fields, solid formulations such as jumbos, packs, granules, and water-dispersible granules, or liquid formulations such as flowables and emulsifiable concentrates are applied usually to flooded paddy fields. In addition, at the time of rice planting, a suitable formulation can be applied onto or injected into soil as it is or after mixed with a fertilizer etc. In addition, the source of water inflow to paddy fields, such as a water inlet and an irrigation system, may be treated with emulsifiable concentrates, flowables, or the like. In this case, the application to paddy fields can be accomplished with the supply of water and thus achieved in a labor-saving manner.

For field crops, their seeds, growing media in the vicinity of their plants, or the like may be treated with the agricultural or horticultural insecticide of the present invention in the period from seeding to seedling culture. In the case of plants for direct-seeding cultivation in the field, direct seed treatment is preferable, and plant foot treatment during cultivation is also preferable. Specifically, granule application or drench treatment with a formulation in a water-diluted or undiluted liquid form can be performed. Another preferable treatment is incorporation of granules into growing media before seeding.

In the case of plants for transplant cultivation, preferable examples of the treatment in the period from seeding to seedling stage include direct seed treatment; drench treatment of nursery beds for seedlings with a formulation in a liquid form; and granule application to nursery beds for seedlings. Also included are treatment of planting holes with granules at the time of fix planting; and incorporation of granules into growing media in the vicinity of transplanting points at the time of fix planting. The agricultural or horticultural insecticide of the present invention is commonly used as a formulation convenient for application, which is prepared by the usual method for preparing agrochemical formulations. That is, the condensed heterocyclic compound having a sulfonamide group represented by the general formula (1) of the present invention or a salt thereof and an appropriate inactive carrier, and if needed an adjuvant, are blended at an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural or horticultural insecticide or animal ectoparasite or endoparasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carrier include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride: organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carrier include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether: ketones, such as acetone, methyl ethyl ketone, methyl isobutyl ketone, diisobutyl ketone and cyclohexanone: ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil: aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

to Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxy ethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil: anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts. polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, olevi amine hydrochloride, stearvl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binder or the tackifier include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickener include water soluble polymers, such as xanthan gum, guar gum, diutan gum, carboxy methyl cellulose, polyvinyl pyrrolidone, carboxy vinyl polymers, acrylic polymers, starch compounds and polysaccharides; and inorganic fine powders, such as high grade bentonite and fumed silica (white carbon).

Examples of the colorant include inorganic pigments, such as iron oxide, titanium oxide and Prussian blue; and organic dyes, such as alizarin dyes, azo dyes and metal phthalocyanine dyes.

Examples of the antifreezing agent include polyhydric alcohols, such as ethylene glycol, diethylene glycol, propylene glycol and glycerin.

Examples of the adjuvant serving to prevent caking or facilitate disintegration include polysaccharides (starch, alginic acid. mannose, galactose. etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agent include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservative include potassium sorbate and 1,2-benzothiazolin-3-one. Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural or horticultural insecticide of the present invention can be adjusted as needed, and basically, the amount of the active ingredient compound is appropriately selected from the range of 0,01 to 90 parts by weight in 100 parts by weight of the agricultural or horticultural insecticide. For example, in the case where the agricultural or horticultural insecticide is in the form of a dust, a granule, an emulsifiable concentrate or a wettable powder, it is suitable that the amount of the active ingredient compound is 0.01 to 50 parts by weight (0.01 to 50% by weight relative to the total weight of the agricultural or horticultural insecticide).

The application rate of the agricultural or horticultural insecticide of the present invention may vary with various factors, for example, the purpose, the target pest, the growing conditions of crops, the tendency of pest infestation, the weather, the environmental conditions, the formulation, the application method, the application site, the application timing, etc. but basically, the application rate of the active ingredient compound is appropriately selected from the range of 0.001 g to 10 kg, preferably 0.01 g to 1 kg per 10 ares depending on the purpose. Furthermore, for the expansion of the range of target pests and the appropriate time for pest control, or for dose reduction, the agricultural or horticultural insecticide of the present invention can be used after mixed with other agricultural or horticultural insecticides, acaricides, nematicides, microbicides, biopesticides and/or the like. Further, the agricultural or horticultural insecticide can be used after mixed with herbicides, plant growth regulators, fertilizers and/or the like depending on the situation.

Exemplary additional agricultural or horticultural insecticides, acaricides and nematicides used for the above-mentioned purposes include 3,5-xylyl methylcarbamate (XMC), fenobucarb (BPMC), Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, acynonapyr, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isanudofos, isoamidofos isoxathion, isocycloseram, isofenphos, isoprocarb (MIPC), epsilon-metofluthrin, epsilon-momfluorothrin, ivermectin, iMucyafos, imidacloprid, imiprothrin indoxacarb, esfenvalerate, ethiofencarb, ethion, ethiprole, etoxazole, ethofenprox, ethoprophos, etrimfos, emanectin, emamectin-benzoate, endosulfan, empenthrin, oxazosulfyl, oxamyl, oxydemeton-methyl, oxydeprofos (ESP), oxibendazole, oxfendazole, potassium oleate, sodium oleate, cadusafos. kappa-tefluthrin, kappa-bifenthrin, cartap, carbaryl, carbosulfan, carbofuran, gamra-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, kelthane (dicofol), salithion, cyhalodiamide, cyanophos (CYAP), diafenthiuron, diamidafos, cyantraniliprole, theta-cypermethrin, dienochlor, cyenopyrafen, dioxabenzofos, diofenolan, sigma-cypernethrin, cyclaniliprole, dichlofenthion (ECP), cycloprothrin, dichlorvos (DDVP), dicloromezotiaz, disulfoton, dinotefuran, cyhalodiamuide, cvhalothrin, cyphenothrin, cyfluthrin, diflubenzuron, cyflumetofen, diflovidazin, cyhexatin, cypermethrin, dimethylvinphos, dimethoate, dinpropyridaz, dimefluthrin, silafluofen, cyromazine, spinetoram, spinosad, spirodiclofen, spirotetramat, spiropidion, spiromesifen, sulfluramid, sulprofos, sulfoxaflor, zeta-cypermethrin, diazinon, tau-fluvalinate, dazomet, thiacloprid, tiaxazafen, thiamethoxam, ioxazafen, thiodicarb, thiocyclam, thiosultap, thiosultap-sodium, thionazin, thiometon, deet, dieldrin, tetrachlorantraniliprole, tyclopyrazoflor, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, doramectin, tralopyril, tralomethrin, transfluthrin, triazamate, triazuron, trichlamide, trichlorphon (DEP), triflumezopyriurm, triflumuron, toifenpyrad, naled (BRP), nithiazine, nitenpy ram, nov aluron, noviflumuron, hydroprene, vaniliprole, varnidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrinmidifen, pyriminostrobin, piririphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrirm fluazaindolizine, fluazinam, fluazuron, fluensulfone, fluxametanide, flucycloxuron, flucythrinate, fluvalinate, flupyradifurone, flufiprole, flupyrazofos, flupyrimin, flufenerim, flufenoxystrobin, flufenoxuron, flufenzine, flufenprox, fluproxyfen, flubrocythrinate, fluhexafon, flubendiamide, flurnethrin, flurimfen, prothiofos, protrifenbute, flonicamid, propaphos, propargite (BPPS), profenofos, broflanilide, profluthrin, propoxur (PHC), flometoquin, alpha-bromadiolone, bromopropylate, beta-cvfluthrin, hexaflumuron, hexythiazox. heptafluthrin, heptenophos, permethrin, benclothiaz, bendiocarb, benzpyrimoxan, bensultap, benzoximate, benfuracarb, phoxim, phosalone, fosthietan, phospharnidon, phosphocarb, phosmet (PMP), polynactins, formothion, phorate. machine oil, malathion, milbemycin, milbemycin-A, milbemectin, mecarbam, mesulfenfos, mrethomyl, metaldehyde, metaflumizone, methaindophos, rnetan-anmnoniur, metam-sodium, methiocarb, methidathion (DMTP), methylisothiocyanate, methylneodecanamide, methylparathion, metoxadiazone, methoxychlor. methoxyfenozide, metofluthrin. methoprene, metolcarb, meperfluthrin, mevinphos, monocrotophos, monosultap, momfluorothrin, lambda-cyhalothrin, ryanodine, lufenuron, rescalure, resmethrin, lepirnectin, rotenone, levarnisole hydrochloride. fenbutatin oxide, morantel tartarate, methyl bromide, tricyclohexyltin hydroxide (cyhexatin), calcium cyanamide, calcium polysulfide, sulfur and nicotine-sulfate, and salts thereof.

Exemplary agricultural or horticultural microbicides used for the same purposes as above include aureofungin, azaconazole, azithiram, acypetacs, acibenzolar, acibenzolar-S-methyl, azoxystrobin, anilazine, amisulbrom, aminopyrifen, ampropylfos, ametoctradin, allyl alcohol, aldimorph, amobam, isotianil, isovaledione, isopyrazam, isofetanid, isoflucypram, isoprothiolane, ipconazole, ipfentrifluconazole, ipflufenoquin, iprodione, iprovalicarb, iprobenfos, imazalil, iminoctadine, metarn, irninoctadine-albesilate, iminoctadine-triacetate, imibenconazole, inpyrfluxam. uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-S-quinolinolate, oxytetracycline, copper-oxinate, oxpoconazole, oxpoconazole-fumarate, oxolinic acid, octhilinone, ofurace, orysastrobin, metan-sodiun, kasugamycin, carbarorph, carpropamid, carbendazim, carboxin, carvone, quinazamid, quinacetol, quinoxyfen, quinofumelin, chinomethionat, quinornethionate, captafol, captan, kiralaxyl, quinconazole, quintozene, guazatine, cufraneb, cuproban, coumoxystrobin, glyodin, griseofulvin, climbazole, cresol, kresoxim-methyl, chlozolinate, clotrimazole, chlobenthiazone, chlocraniformethan, chloranil, chlorquinox, chloropicrin, chlorfenazole, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, dichlofluanid, cycloheximide, dichlobentiazox, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipymetitrone, dipyrithione, diphenylamrine, difenoconazole, cy flufenarid, diflumetorim, cyproconazole, cyprodinil, cyprofuram, cypendazole, simeconazole, dimethirimol, dimethomorph, cymoxanil, dimoxystrobin, ziram, silthiofam.

streptomycin, spiroxamine, sultropen, sedaxane, zoxamide, dazomet, thiadiazin, tiadinil, thiadifluor, thiabendazole, tioxymid, thioquinox, thiochlorfenphim, thiophanate, thiophanate-nmethyl, thifluzamide, thicyofen, thioquinox, thiram, decafentin, tecnazene, tecloftalam, tecoram, tetraconazole, debacarb, dehydroacetic acid, tebuconazole, tebufloquin, dodicin, dodine, dodecyl benzensulfonate bisethylene diamine copper(11) (DBEIDC), dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, tnifloxystrobin, triforine, tolyfiuanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, picarbutrazox, bixafen, picoxystrobin, picobenzamide, pydiflumetofen, bithionol, bitertanol, hydroxyisoxazole. hydroxyisoxazole-potassinut, binapacryl, biphenyl, piperalin, hymexazol, pyraoxystrobin, pyracarboiid, pyraclostrobin, pyraziflumid, pyrazophos, pyrapropoyne, pyrametostrobin, pyriofenone, pyridinitril, pyrifenox, pyrisoxazole, pyridachlometyl, pyrifenox, pyribencarb, pvriminostrobin, pyrimethanil, pyroxy chlor, pyroxyfur, pyroquilon, vinclozolin, ferbam, famoxadone, fenapanil, fenamidone, fenaminosulf, fenaminstrobin, fenarimol, fenitropan, fenoxanil, ferimzone, ferbam, fentin, fenpiclonil, fenpicoxamid, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluindapyr, fluoxastrobin, fluoxapiprolin, fluotrimazole, fluopicolide, fluopimornide, fluopyram, fluoroimide, furcarbanil, fluxapyroxad, fluquinconazole, furconazole, furconazole-cis, fludioxonil, flusilazole, flusulfamide, flutianil, flutolanil, flutriafol, flufenoxystrobin, furfural, furmecyclox, flumetover, flumorph, proquinazid, prochloraz, procymidone, prothiocarb, prothioconazole, pronitridine, propamocarb, propiconazole, propineb, furophanate, probenazole, bromuconazole, florylpicoxamid, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, benzovindiflupyr, bentaluron, benthiazole, benthiavalicarb, benthia.valicarb-isopropyl, penthiopyrad, penflufen, boscalid, phosdiphen, fosetyl, fosety-A1, polyoxins. polyoxorim, polycarbamate, folpet, formaldehyde, machine oil, maneb, mancozeb, mandipropamid, mandestrobin, myclozolin, myclobutanil, mildiomnycin, milneb, mecarbinzid, methasulfocarb, metazoxolon, metam, metamsodiun, metalaxyl, metalaxyl-M. metiram, methyl isothiocyanate, meptyldinocap, meyltetraprole, metconazole, metsulfovax, methfuroxam, metominostrobin, metrafenone, mepanipyrim, mefenoxam, mefentrifluconazole, meptyidinocap, mepronil, mebenil, iodomethane, rabenzazole, methyl bromide. benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate, and salts thereof.

Exemplary herbicides used for the same purposes as above include 1-naphthylacetamide, 2,4-PA, 2,3,6-TBA, 2,4,5-T, 2,4,5-TB, 2,4-D. 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, acionifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprynuidam, imazaquin, imazapic, imazapyr, imazamethapy r, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyi, ethalfluralin, ethiolate, ethvchlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, orvzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlometboxynil, chlomethoxyfen, clomeprop, chlorazifop, chlorazine, cloransulam, chloranocryl, chloramben, cloransulam, cloransulan-methyl, chloridazon, chlorinuron, chlorimuron-ethyl, chlorsulfuron, chlorthal, chlorthiamid, chlortoluron, chloritrofen, chlorfenac, chlorfenprop, chlorbufain, chlorphthalin, chlorflurazole, chlorfiurenol, chlorprocarb, chlorpropham, chlormequat, chloreturon, chloroxynil, chloroxuron, chlorotoluron, chloropon, saflufenacil, cyanazine, cyanatryn, di-allate, diuron, diethamquat, dicamba, cycluron, cycloate, cycloxydim, diclosulan, cyclosulfamuron, cyclopyranil, cyclopyrimorate, dichlorprop, dichlorprop-P, dichlobenil, diclofop, diclofop-imethyl, dichlormate, dichloralurea, diquat, cisanilide, disul, siduron, dithiopyr, dinitramine, cinidon-ethyl, dinosan cinosulfuron, dinoseb, dinoterb, dinofenate, dinoprop, cyhalofop-butyl, diphenamid, difenoxuron, difenopenten, difenzoqual, cybutryne, cyprazine, cyprazole, diflufenican, diflufenzopyr, dipropetryn, cypromid, cyperquat, gibberellin, simazine, dimexano, dimethachlor, dimidazon, dirnethametryn, dimethenarmid, simetryn, sirneton, dimepiperate, dirnefuron, cinmethylin, swep, sulglycapin, sulcotrione, sulfallate, sulfentrazone, sulfosulfuron, sulfoneturon, sulfometuron-methyl, secbumeton, sethoxydim, sebuthylazine, terbacil, daimuron, dazormet, dalapon, thiazafluron, thiazopyr, tiafenacil, thiencarbazone, thiencarbazone-methyl, tiocarbazil, tioclorim, thiobencarb, thidiazinin, thidiazuron, thifensulfuron, thifensulfuron-me-thyl, desmedipham, desmetryn, tetflupyrolimet, tetrafluron, thenylchlor, tebutarn, tebuthiuron, terbumeton, tepraloxydim, tefuryltione, tembotrione, delachlor, terbacil, terbucarb, terbuchlor, terbuthylazine, terbutryn, topramezone, tralkoxydin, triaziflam, tiasulfuron, triafarnone, tri-allate, trietazine, tricamba, triclopyr, tridiphane, tritac, tritosulfuron, trifludirnoxazin, triflusulfuron, triflusulfuron-methyl, trifluralin, trifloxysulfuron, tripropindan, tribenuron, tribenuron-methyl, trifop, trifopsime, trimeturon, tolpyralate, naptalan, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, baloxyfop, haloxyfop-P, haloxyfopmethyl, halosafen, halosulfuron, halosulfuron-methyl, bilanafos, bixlozone, picloram, picolinafen, bicyclopyrone, bispyribac, bispyribac-sodium, pydanon, pinoxaden, bifenox, piperophos, hyrexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulanm, fenasulan, phenisopharn, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin. butroxy dim, flazasulfuron, flanmprop, furyloxyfen, pry, nachlor, primisulfuron-methyl, fluazifop, fluazifop-P, fluazifop-butyl, fluazolate, fluroxypyr, fluothiuron, fluorneturon, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, fluniclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, proflurahn, probexadione-calcium, propoxycarbazone, propoxycarbazone-sodium, profoxydim, bromacil, brompyrazon, prometryn, prometon, bromoxynil, bromofenoximu, bromobutide, bromobonil, florasulam, florpyrauxifen, hexachloroacetone, hexazinone, pethoxamid, benazolin, penoxsulam, pebulate, beflubutamuid, beflubutamid-M, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic bydrazide, mec-oprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metarm, methalpropalin, methiuron, methiozolin, methiobencarb, methyldynron, metoxuron, metosulam, metsulfuron, metsulfuron-methyl, metflurazon, metobromuron, metobenzuron, methometon. metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rinsulfuron, lenacil, rhodethanil, calcium peroxide and methyl bromide, and salts thereof Examples of the biopesticide include Agrobacterjum *radiobacter* (e.g., Galltrol-A (registered trademark) manufactured by AgBioChem, CA using strain K84 and Nogall (registered trademark) manufactured by Becker Underwood, US using strain K1026), *Agrobacterium radiobacter* (e.g., Bacterose (registered trademark) manufactured by NIHON NOHYAKU Co, Ltd. using strain 84), Anpelomyces quisquahs (e.g., AQ 10 (registered trademark) manufactured by IntrachernBio Italia & Co. KG using strain AQ10), *Aspergillus;*7avus (e.g., A fla-Guard (registered trademark) manufactured by Syngenta, AF36 (registered trademark) manufactured by Arizona Cotton Research and Protection Council, US using strain AF36, and Afla-Guard manufactured by Syngenta using NRRL 21882), Aureobasidiuni pullutans (e.g., Botector (registered trademark), a mixture of blastospores of strain DSM14940 and blastospores of strain DSM14941, manufactured by bio-ferm, GmbH),

*Bacillus* anyloiiqueJbciens (e.g., Impression Clear (registered trademark) manufactured by Idemitsu Agri using strain AF-332, Avogreen (registered trademark) manufactured by University of Pretoriar using strain B246, Bacstar (registered trademark) manufactured by Etec Crop Solutions, NZ using strain D747, Shelter (registered trademark) manufactured by Dagutat Bio lab, ZA using strain DB101, Artemis (registered trademark) manufactured by Dagutat Bio lab, ZA using strain DB102, RhizoVital (registered trademark) manufactured by ABiTEP, DE using strain FZB42, Kodiak (registered trademark) manufactured by Bayer CropScience AG, DE using strain GB03. Subtilex (registered trademark) manufactured by Becker Underwood, US using strain MBI600, and Amplitude manufactured by Marrone Bio Innovations, Inc. using strain F727), *Bacillus cepacia* (e.g., Deny Stine (registered trademark) manufactured by Microbial Products), *Bacillus cereus* (e.g., Mepichlor (registered trademark) manufactured by Arysta. US using strain BPO1), *Bacillus* firnus (e.g., BioNeem (registered trademark) manufactured by AgoGreen using strain 1-1582), *Bacillus* lacticola (e.g., a product manufactured by Micro Flo Company), *Bacillus* lactinorbus (e.g., a product manufactured by Micro Flo Company), *Bacillus lactis* (e.g., a product manufactured by Micro Flo Company), *Bacillus* lacrosporus (e.g., Bio-Tode (registered trademark) manufactured by Agro-Organics, SA), *Bacillus* lichenilorniis (e.g., EcoGuard Biofungicide (registered trademark) manufactured by Novozymes using strain SB3086), Baciilus *maroccanus* (e.g., a product manufactured by Micro Flo Company), *Bacillus* mecgaterium (e.g., Bioarc (registered trademark) manufactured by Bio Arc using strain YFM3.25), *Bacillus* metiens (e.g., a product manufactured by Micro Flo Company), *Bacillus mojavensis* (e.g., a product manufactured by Probelte, Sa using strain SR11), *Bacillus* nycoides (e.g., BmJ (registered trademark) manufactured by Certis USA using isolate J.), *Bacillus* nigrillcans (e.g., a product manufactured by Micro Flo Company), *Bacillus* popillae (e.g., Cronox (registered trademark) manufactured by Bio Crop, CO), *Bacillus pumilus* (e.g., Integral F-33 (registered trademark) manufactured by Becker Underwood, US using strain BU F-33, Yield Shield (registered trademark) nanufactured by Bayer CropScience AG, DE using strain GB34, and Sonata (registered trademark) manufactured by Bayer CropScience LP, US using strain QST2808), *Bacillus simplex* (e.g., Momi-Hope WP (registered trademark) manufactured by Arysta LifeScience Corporation using strain CGF2856), *Bacillus sphaericus* (e.g., VectoLex (registered trademark) manufactured by Valent BioSciences, US using serotype H5a5b strain 2362), *Bacillus* subtiiis (e.g., Botokiller WP (registered trademark) manufactured by Idemitsu Agri Co, Taegro (registered trademark) manufactured by Novozyme Biologicals, Inc. US using strain FZB24, SERENADE MAX (registered trademark) manufactured by Bayer CropScience LP, US using strain QST713/AQ713, Serenade-DPZ (registered trademark) using strain AQ30002, EcoShot (registered trademark) manufactured by KUTMIAI CHEMICAL INDUSTRY Co, Ltd. using strain D747, Agrocare WP (registered trademark) manufactured by Nisso Green Co, Ltd. using strain HAI-0404, Botopika WP (registered trademark) manufactured by Idemitsu Kosan Co, Ltd. using strain MB1600, BaciStar WP (registered trademark) manufactured by Arysta. LifeScience Corporation using strain Y1336, and Companion Biological Fungicide Wettable Powder manufactured by Growth Products Ltd. using strain GB03), *Bacillus thuringiensis* (e.g., VectoBac (registered trademark) manufactured by Valent BioSciences, US using strain AM65-52), *Bacillus* ihuringienses a;zawai (e.g., XenTari (registered trademark) manufactured by Bayer CropScience AG, DE using strain ABTS-1857, Florbac WG (registered trademark) manufactured by Valent BioSciences, US using serotype H-7 and Agree WG Biological Insecticide manufactured by Certis USA using strain GC-91), *Bacillus thuringiensis* subspecies. Aegvpti (e.g., Agerin (registered trademark)), *Bacillus* thuringienses *israelensis* (e.g. Aquabac (registered trademark) manufactured by Becker Microbial Products IL using strain BMP144), *Bacillus* thuringienses kurstaki (e.g., a product manufactured by Becker Microbial Products, IL using strain BMP 123, Dipel ES (registered trademark) manufactured by Valent BioSciences, US using strain HD-1. BMP 123 manufactured by Becker Microbial Products using strain BMP123, BMP144/Aquabac manufactured by Becker Microbial Products using strain BMP144, Dipel 10G manufactured by Valent U.S.A. LLC using strain ABTS-351, Condor Wettable Powder manufactured by Certis USA using strain EG2348, Crymax Bioinsecticide manufactured by Certis USA using strain EG7841, Deliver Biological Insecticide manufactured by Certis USA using strain SA-12, and Bioprotec PLUS manufactured by AEF Global using strain EVB-113-19), *Bacillus* thuringietsis galleriae (e.g., beetleGONE manufactured by Phylom BioProducts and boreGONEl manufactured by Phylom BioProducts using strain SDS-502), *Bacillus thuringiensis* var, colmeri (e.g., TianBaoBTc (registered trademark) manufactured by Changzhou Jianghai Chemical Factory), *Bacillus* thuringienses tenebrionis (e.g., Novodor FC (registered trademark) manufactured by BioFa DE using strain NB 176), *Bacillus* thurigiensis var, san diego (e.g., M-One (registered trademark) from *Bacillus thuringiensis* var, san diego),

*Beauveria bassiana* (e.g., Naturalis (registered trademark) manufactured by Intrachem Bio Italia, Bove Max (registered trademark) manufactured by Novozymes using strain CG716, BioLisa Madara (registered trademark) manufactured by Idemitsu Kosan Co, Ltd. using strain F-263, BotaniGard WP (registered trademark) manufactured by ARYSTA using strain GHA, balEnce manufactured by Terragena, Inc. using strain HF23, BotaiGard ES manufactured by BioWorks Inc. using strain GIA, and BioCeres WP manufactured by BioSafe Systems using strain ANT-03), *Beauveria* brongnioartii (e.g., Beaupro (registered trademark) manufactured by Andermatt Biocontrol AG), Brad. *rhizobium japonicum* (e.g., Optimize (registered trademark) manufactured by Novozymes), *Burkholderia* spp, (e.g., MBI-206 TGAI (registered trademark) manufactured by Marrone Bio Innovations using strain A396),

*Candida* oleolphila (e.g., Aspire manufactured by Ecogen Inc, US using strain 1-82 and Nexv manufactured by BioNext using strain 0). Canidida *saitoana* (e.g. BIOCURE (registered trademark) manufactured by Micro Flo Company, US (BASF SE)), Chaetoiniun cupreum (e.g., BIOKUPRUNM (registered trademark) manufactured by AgriLife), Chaeromium giobosum (e.g., Rivadiom (registered trademark) manufactured by *Rivale*), Chromobacterium subtsugae (e.g., Grandevo (registered trademark) manufactured by Marrone Bio Innovations using strain PRAA4-IT), Cladosporiumz cladosporioides (e.g., from *Cladosporium* cladosporioides), CIonostachys *rosea* f. *catenulate* (e.g., PRESTOP (registered trademark) manufactured by Verdera, Finland using strain J1446), Colletotrichun gioeosporioides (e.g., Collego (registered trademark) manufactured by Agriultural Research Initiatives), Coniothrrum Mmitans (e.g., Contans (registered trademark) manufactured by Encore Technologies, LLC using strain CON/M/91-08), *Cryptococcus albidus* (e.g., YieldPlus (registered trademark) manufactured by Anchor Bio Technologies, ZA), Dellia *acidovorans* (e.g., BioBoost (registered trademark) manufactured by Brett Young Seeds using strain RAY209). Dilophosphora alopecuri (e.g., Twist Fungus (registered trademark)), Drechsrela *monoceras* (e.g., Tasumato herbicide (registered trademark) manufactured by Mitsui Chemicals Agro, Inc. using strain MTB-951), *Entomophthora* virulenta (e.g., Vektor (registered trademark) manufactured by Ecomic), Fusariurn *oxysporum* (e.g., Maruka light manufactured by Eisai Seikaken, Inc. using strain 101-2). Fusariunm *oxysporum* (e.g., Fusaclean (registered trademark) manufactured by Natural Plant Protection using strain Fo47), Ghiocladiurn spp, (e.g., Prestop (registered trademark) manufactured by AgBio Inc. using strain J1446 and a product manufactured by WF. Stoneman Company LLC using strain 3211U), Hirsute/la trhompsonii (e.g., Mycohit (registered trademark) manufactured by Agro Bio tech Research Centre. IN), *Lactobacillus acidophilus* (e.g., Fruitsan (registered trademark) manufactured by Inagrosa Industrias Agrobiologicas. S. A.), Lacrobacillus plantarurn (e.g., Lactoguard WP manufactured by Meiji Seika Pharma Co, Ltd. using strain BY), Lecanicilliun lecanii (e.g., Mycotal (registered trademark) manufactured by koppert/Arysta using conidiospores of strain KV01), Metarhizium anisopliae (e.g., BIO 1020 (registered trademark) manufactured by Bayer CropScience using strain F52, Pirates G (registered trademark) mnanufactured by Arysta LifeScience Corporation using strain SM Z-2000, and Bio-Blast manufactured by LidoChem Inc using strain ESCI) Metarhizunz anisoplae var, acridumw (e.g., Green Muscle (registered trademark) manufactured by Biological Control Products and GreenGuard (registered trademark) manufactured by Becker Underwood, US), Merschnikowia fructicola (e.g., Shemer (registered trademark) manufactured by Bayer CropScience), Micraciochiurn diinerun (e.g., ANTIBOT (registered trademark) manufactured by Agrauxine, France), Miicrosphaeropsis achracea (e.g., Microx (registered tradernark) manufactured by Prophyta), Monacrosporiurnphynatopagun (e.g., Nemahiton (registered trademark) manufactured by Tomrioe Kagaku Kogyo K.K.). XMucor haenelis (e.g., BioAvard (registered trademark) manufactured by Indore Biotech Inputs & Research), Muscodor *albus* (eg, Arabesque manufactured by Bayer Crop Science using strain QST 20799),Myrtheciurn verrucaria (e.g., DiTera (registered trademark) manufactured by Valent Biosciences using strain AARC-0255), Paecilorycesfiaosoroseus (e.g., PreFeRal (registered trademark) WG manufactured by Biobest using strain apopka 97, Preferred WP manufactured by Tokai Bussan Co. Ltd, and No Fly (registered trademark) manufactured by Natural Industries Inc, (Novozymes company) using strain FE 9901), Paeciiomvyces *lilacinus* (e.g., BioAct WG (registered trademark) manufactured by Prophyia using strain 251) PaciliRyces *tenuipes* (e.g., GottuA manufactured by Idemitsu Kosan Co, Ltd. using strain T1), Paeciloryces *variotii* (e.g., Nemaquim (registered trademark) manufactured by Quimia, MX using strain Q-09), Paenihacillus poynxa (e.g., Topseed (registered trademark) manufactured by Green Biotech Company Ltd. using strain AC-1), *Paenibacillus* poppiliae (e.g., Milky spore disease (registered trademark) manufactured by St. Gabriel Laboratories), Pasteuria nishizawae (e.g., oyacyst LF/ST (registered trademark) manufactured by Pasteuria Bioscience and Clariva pn manufactured by Syngenta using strain Pnl), Pasteuria *penetrans* (e.g., Pasteuria (registered trademark) manufactured by Pasteuria Bioscience), Pasteuria usagae (e.g., Econem (registered trademark) manufactured by Pasteuria Bioscience), Pantoa aggianerans (e.g., Bloomtime Biological FD Biopesticide manufactured by Nufann US using strain E325), Pectobacteriun carotavarurM (e.g., Biokeeper (registered trademark) manufactured by Nissan Chemical Corporation and EcoMate (registered trademark) manufactured by KUMIAI CHEMICAL INDUSTRY Co, Ltd. using CGE234M403), Phona macrostrona (e.g., *Phoma* H (registered trademark) manufactured by Scotts, US usina strain 94-44B), Penicilium bilali (e.g., Jump Start (registered trademark) manufactured by Novozymes), *Phlebiopsis* gigantea (e.g., ROTSOP (registered trademark) manufactured by Verdera, Finland using strain FOC PG B22/SP1190/3.2), Pochonia chiamydosporia var, catenuiata (e.g., KlamiC (registered trademark) manufactured by The National Center of Animal and Plant Health (CENSA); CU), Pseaudomonas aureoaicens (e.g., Spot-Less Biofungicide (registered trademark) manufactured by Eco Soils Systems, CA using strain TX-1). *Pseudomonas chlororaphis* (e.g., ATEze (registered trademark) manufactured by EcoSoil Systems using strain 63-28 and Cedomon (registered trademark) manufactured by Bioagri, S. using strain MA 342), *Pseudomonas* fuorescens (e.g., Frostban D (registered trademark) manufactured by Frost Technology Corp. using strain 1629RS, Blightban (registered trademark) manufactured by Blightban using strain A506, Konae *Fukudo* (registered trademark) manufactured by Taki Chemical Co, Ltd. using strain FPT-9601, Cell Nae Gienki (registered trademark), a mixture of strains FPT-9601 and FPH-9601, manufactured by Taki Chemical Co, Ltd, and Vegikeeper (registered trademark) manufactured by Arysta LifeScience Corporation using strain G7090), *Pseudomonas* proradix (e.g.. Proradix (registered trademark) manufactured by Sourcon Padena), Pseudononas *resinovorans* (e.g., Solanacure (registered trademark) manufactured by Agricultural Research Council, SA), *Pseudomonas syringae* (e.g., Biosave (registered trademark) manufactured by EcoScience, US using strain MA-4, Frostban C (registered trademark) manufactured by Frost Technology Corp using strain 742RS, Biosave 10LP Biological Fungicide manufactured by Jet Harvest Systems using strain ESC10, and Bio-Save 1ILP Biological Fungicide manufactured by Jet Harvest Systems using strain ESCl1), *Pseudomonas* spp, (e.g., Masterpiece WP (registered trademark) manufactured by Nippon Soda Co, Ltd. using strain HAI-0804 and Momi-Genki WP manufactured by Nissan Chemical Corporation using strain CAB-02), Pseudoz ma ap.hidis (e.g., a product manufactured by Yissum Research Development Company of the Hebrew University of Jerusalem), Pseudozymaflocculosa (e.g., Sporodex L manufactured by Plant Products Co. Ltd, CA using strain PF-A22 UL), *Pythium* ohgandrum (e.g., Polyversum (registered trademark) manufactured by Bioprepratv, CZ using strain DV74 or strain M1), *Reynoutria* sachlinensis (e.g. REGALIA (registered trademark) manufactured by Marrone BioInn ovations, US), Rhizopogon anylopogon (e.g., Myco-Sol (registered trademark) manufactured by Helena Chemical Company), Rhizopogon fulvigleba (e.g., Myco-Sol (registered trademark) manufactured by Helena Chemical Company),

*SaccharomYces cerevisiae* (e.g., a product manufactured by i.esaffre et Compagnie, FR), *Sclerotinia* minor (e.g., Sarritor (registered trademark) manufactured by Agrium Advanced Technologies), *Serratia* entornophia (e.g., Invade (registered trademark) manufactured by Wrightson Seeds), *Sporothrix* insectorum (e.g., *Sporothrix* Es (registered trademark) manufactured by Biocerto, BR), Steinernema carpocapsae (e.g. Biosafe (registered trademark) manufactured by SDS Biotech K. K.), Steinernena tushidai (e.g., Shibaichi-Nema rnanufac(tired by Kubota Corporation), Sieinernema glaseri (e.g. Biotopia (registered trademark) manufactured by Arysta LifeScience Corporation), *Streptomyces acidiscabies* (e.g., MBI-005EP (registered trademark) manufactured by Marrone Bioinnovations, CA using strain RL-110T), Streptonyces *candidus* (e.g., BioBac (registered trademark) manufactured by Biontech, TW using strain Y21007-2), Streptomnyces goiaus (e.g., Mycostop (registered tradenark) manufactured by Verdera using strain K61), Streptonyces hydicus (e.g., ACTINOVATE (registered trademark) manufactured by Natural Industries, US using strain WYEC108), Strepromyces saraceticus (e.g., Clanda (registered trademark) manufactured by A & A Group (Agro Chemical Corp.)),

*Talaromyces flavus* (e.g., Momi-keeper (registered trademark) manufactured by Central Glass Co, Ltd. using strain B-422, Tough Block (registered trademark) manufactured by Idemitsu Kosan Co, Ltd. using strain SAY-Y-94-01, and PROTUS (registered trademark) WG manufactured by Prophyta, DE using strain V117b), *Trichoderma* aspereillm (e.g., a product manufactured by Isagro using strain TCC 012, T34 Biocontrol (registered trademark) manufactured by Bioncontrol Technologies, ES using strain T34, and Eco-Hope (registered trademark) manufactured by KUMIAl CHEMICAL INDUSTRY Co, Ltd. using strain SKT-1), *Trichoderma* atroviride (e.g., Esquive (registered trademark) WP manufactured by Agrauxine. FR, Tenet (registered trademark) manufactured by Agrimm Technologies Ltd. NZ or SENTINEL (registered trademark) each using strain LC52, and EcoHope DJ (registered trademark) manufactured by KUMTAI CHEMICAL INDUSTRY Co, Ltd. using strain SKT-1), *Trichoderma* gansii (e.g., BIO-TAM (registered trademark) manufactured by Bayer CropScience LP, US), *Trichoderma* harzianun, (e.g., T-Gro 7456 (registered trademark) manufactured by Dagutat Biolab using strain DB 103, Trianum-P (registered trademark) manufactured by Koppert using strain ITEM908, Trichoplus (registered trademark) manufactured by Biological Control Products, SA using strain KD, and ROOT PRO (registered trademark) manufactured by Mycontrol Ltd. using strain TH-35), Trichodernma harzianun Rifai (e.g., PLANTSHIELD T-22G (registered trademark) manufactured by *Firma* BioWorks Inc, US using strain T-22 and TRICHODEX (registered trademark) manufactured by Makhteshim Ltd, US using strain T-39), *Trichoderma* Iignorum (e.g., Mycotric (registered trademark) manufactured by Futureco Bioscience, ES using strain TL-0601), Trichodernapolysporun (e.g., Binab TF WP (registered trademark) manufactured by BINAB Bio-Innovation AB, Sweden), DRichodermia stromaticun (e.g., TRICOVAB (registered trademark) manufactured by Ceplac, Brazil), Trichoderna *virens* (e.g., SOILGARD (registered trademark) manufactured by Certis LLC, US using strain GL-21), 7richoderma *viride* (e.g., REMEDIER (registered trademark) WP manufactured by Isagro Ricerca, ITALIA using strain ICC080 and TrianuimP (registered trademark) manufactured by Koppert using strain TV1).

Tsukamurella paurometabola (e.g., HeberNem (registered trademark) using strain C-924), Ulocladiuni oudemzansii (e.g., Botry-Zen (registered trademark) rnanufactured by Botry-Zen Ltd, NZ using strain HRU3 and BotryStop manufactured by BioWorks Inc. using strain U3), Kriovorax

*paradoxus* (e.g., Fieldkeeper WP (registered trademark) manufactured by Central Glass using strain CGF4526), Vesicular-Arbuscular (VA) mycorrhizal fungi (e.g., Dr Kinkon (registered trademark) manufactured by Idemitsu Agri), Verticidliw alboatrum (e.g., Dutch Trig (registered trademark) manufactured by Tree Care Innovations using strain WCS850), *Verticillium* lecanli (e.g., Vertalec (registered trademark) manufactured by Arysta LifeScience Corporation using strain IMI 179172 and Mvcotal (registered trademark) manufactured by Arvsta LifeScience Corporation using strain IMI 263817), Xanrthononas carnpestris (e.g., Camperico L (registered trademark) manufactured by Taki Chemical), Xanthomionas *campestris* pv. *poae*, HIeterorhabdilis bacterophora, Steinernemna feliae, Steinernema krausset, Steinernema riobrave, and Steinernema scapterisci; and insecticidal and microbicidal strains selected from mutants of the above-listed strains that each have its original distinguishing characteristics, and metabolites that are produced by the above-listed strains and active against plant pathogenic microbes.

Other examples of the biopesticide used in combination with the agricultural or horticultural insecticide of the present invention include natural predators such as Encarsia tormfosa *Aphidius colemani*, Aphidoletes aphidhmyza, Diglyohus isaea, Dacnusa *sibirica*, P ulus persirnlis, Amblyseius cucuneris, and Orius sauteri; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, and 14-methyl-1-octadecene.

Hereinafter, production examples of representative compounds of the present invention and their intermediates will be described in more detail, but the present invention is not limited only to these examples.

EXAMPLES

Example 1

Production of 5-cyclopropyl-N-methyl-2-(3-methyl-6-trifluoromethyl-3H-imidazo [4,5-b]pyridin-2-yl) pyridine-3-sulfonamide (Compound No. 1-1)

[Chem. 14]

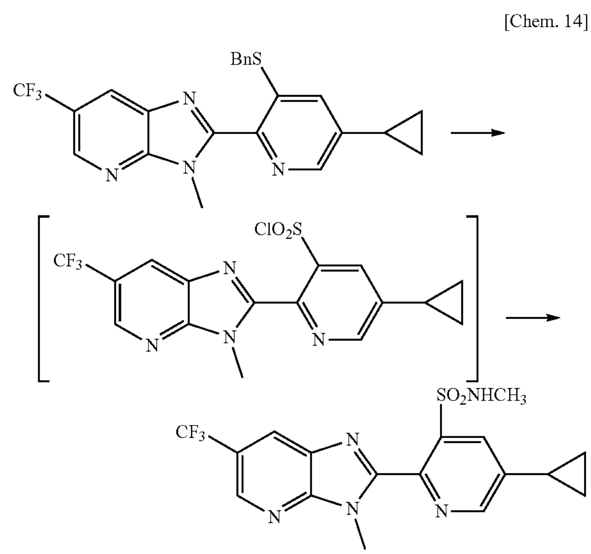

To a solution of 2-(3-benzylthio-5-cyclopropylpyridin-2-yl)-3-methyl-6-trifluoromethyl-3H-imidazo [4,5-b]pyridine (102 mg), which was produced by the method described in Reference Example 1, in a mixed solvent of acetonitrile (2 mL) and acetic acid (0.2 mL), 1,3-dichloro-5,5-dimethylhydantoin (118 mg) was added, and the mixture was allowed to react for 10 minutes to produce a sulfonic acid chloride compound. Without isolating or purifying the sulfonic acid chloride compound, tetrahydrofuran (THF) (3 mL) and a 40 mass % methanol solution (2 mL) of methylamine were added to the reaction mixture, and the mixture was allowed to react for 10 minutes. A saturated aqueous sodium thiosulfate solution and ethyl acetate were added. The organic layer was concentrated, and the residue was subjected to column chromatography to give the desired compound (94 mg). Bn stands for a benzyl group.

EXAMPLE 2

Production of N,N-dimethyl-5-(4-fluorophenyl)-2-(3-methyl-6-(trifluoromethyl-3H-imidazo [4,5-c] pyridazin-2-yl) pyridine-3-sulfonamide (Compound No. 2-3)

[Chem 15]

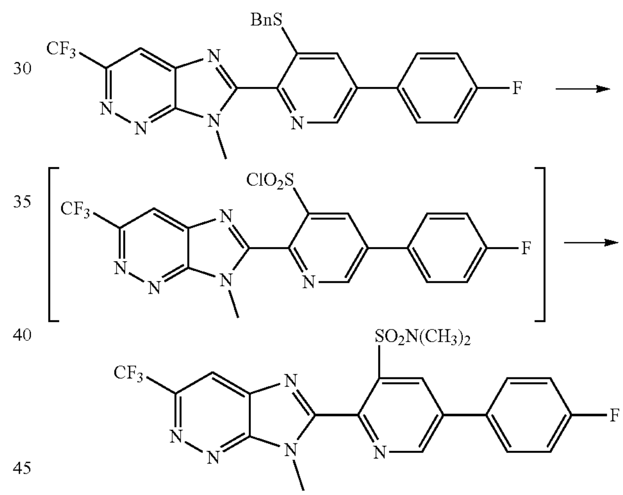

2-(5-(4-Fluorophenyl)-3-ethylsulfonylpyridin-2-yl)-3-methyl-6-trifluoromethyl-3H-imidazo [4,5-c]pyridazine, which was synthesized by the method described in WO 2016/059145, was converted to 2-(5-(4-fluorophenyl)-3-benzylthiopyridin-2-yl)-3-methyl-6-trifluoromethyl-3H-imidazo [4,5-c]pyridazine according to the method described in Reference Example 1. This compound was reacted with 1,3-dichloro-5,5-dimethylhydantoin in a mixed solvent of acetonitrile and acetic acid as described in Example 1 to produce a sulfonic acid chloride compound. Without isolating or purifying the sulfonic acid chloride compound, THF and a 50 mass % aqueous dimethylamine solution instead of the 40 mass % methanol solution of methylamine used in Example 1 were added to the reaction mixture. The mixture was subjected to the same procedure as described in Example 1 to give the desired compound.

EXAMPLE 3

Production of 5-cyclopropyl-N,N-dimethyl-2-(5-trifluoromethylthiobenzoxazol-2-yl) pyridine-3-sulfonamide (Compound No. 4-6)

[Chem. 16]

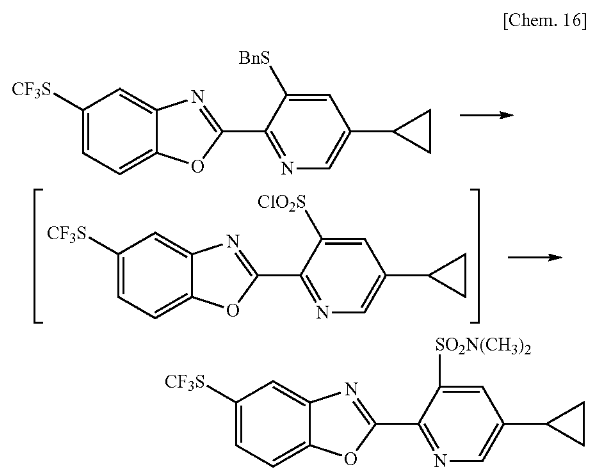

2-(5-Cyclopropyl-3-ethylsulfonylpyridin-2-yl)-5-(trifluoromethylthio) benzoxazole, which was synthesized by the method described in WO2016/121997, was converted to 2-(3-benzylthio-5-cyclopropylpyridin-2-yl)-5-(trifluoromethylthio) benzoxazole according to the method described in Reference Example 1. This compound was reacted with 1,3-dichloro-5,5-dimethylhydantoin in a mixed solvent of acetonitrile and acetic acid as described in Example 1 to produce a sulfonic acid chloride compound. Without isolating or purifying the sulfonic acid chloride compound, THF and a 50 mass % aqueous dimethylamine solution instead of the 40 mass % methanol solution of methylamine used in Example 1 were added to the reaction mixture. The mixture was subjected to the same procedure as described in Example 1 to give the desired compound.

Example 4

Production of N,N-dimethyl-5-(3-trifluoromethylphenyl)-2-(7-trifluoromethyl-1,2,4-triazolo [1,5-a] pyridin-3-yl) pyridine-3-sulfonamide (Compound No. 5-3)

[Chem. 17]

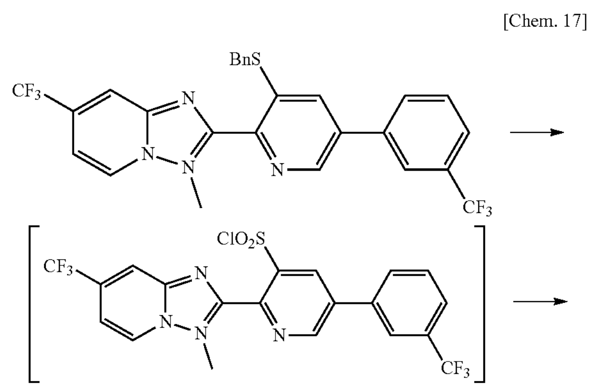

-continued

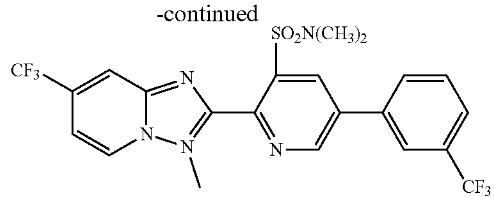

2-(3-Ethylsulfonyl-5-(3-trifluoromethylphenyl) pyridin-2-yl)-7-trifluoromethyl-1,2,4-triazolo [1,5-a]pyridine, which was synthesized by the method described in WO2019/038195, was converted to 2-(3-benzylthio-5-(3-trifluoromethylphenyl) pyridin-2-yl)-7-trifluoromethyl-1,2,4-triazolo [1,5-a]pyridine according to the method described in Reference Example 1. This compound was reacted with 1,3-dichloro-5,5-dimethylhydantoin in a mixed solvent of acetonitrile and acetic acid as described in Example 1 to produce a sulfonic acid chloride compound. Without isolating or purifying the sulfonic acid chloride compound, THF and a 50 mass % aqueous dimethylamine solution instead of the 40 mass % methanol solution of methylamine used in Example 1 were added to the reaction mixture. The mixture was subjected to the same procedure as described in Example 1 to give the desired compound.

Reference Example 1

Production of 2-(3-benzylthio-5-cyclopropylpyridin-2-yl)-3-methyl-δ-trifluoromethyl-3H-imidazo[4,5-b] pyridine

[Chem. 18]

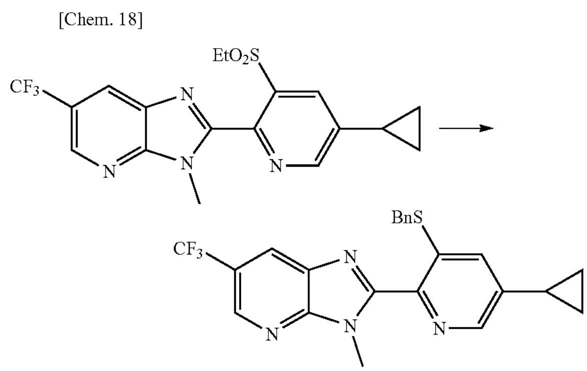

To a DMF (10 mL) solution of 2-(5-cyclopropyl-1,3-ethylsulfone pyridin-2-yl)-3-methyl-δ-trifluoromethyl-3H-imidazo[4,5-b]pyridine (1.13 g), which was produced by the method described in WO2016/121998, benzylthiol (585 μL) and 60 mass % sodium to hydride (220 mg) were successively added under an argon atmosphere. The mixture was stirred at 100° C. for 10 minutes, and water and ethyl acetate were added. The organic layer was concentrated, and the residue was subjected to column chromatography to give the desired compound, i.e. 2-(3-benzylthio-5-cyclopropylpyridin-2-yl)-3-methyl-δ-trifluoromethyl-3H-imidazo[4,5-b] pyridine (0.45 g). Melting point: 140 to 143° C.

Hereinafter, formulation examples in connection with the present invention are shown, but the present invention is not limited thereto. In the formulation examples, "part" means part by weight.

| Formulation Example 1 | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate (volume ratio of 1:1) | 10 parts |

The above ingredients are uniformly mixed for dissolution to give an emulsifiable concentrate formulation.

| Formulation Example 2 | |
|---|---|
| Compound of the present invention | 3 parts |
| Clay powder | 82 parts |
| Diatomite powder | 15 parts |

The above ingredients are uniformly mixed and then pulverized to give a dust formulation.

| Formulation Example 3 | |
|---|---|
| Compound of the present invention | 5 parts |
| Mixture of bentonite powder and clay powder (volume ratio of 1:1) | 90 parts |
| Calcium lignosulfonate | 5 parts |

The above ingredients are uniformly mixed. After addition of an appropriate volume of water, the mixture is kneaded, granulated and dried to give a granular formulation.

| Formulation Example 4 | |
|---|---|
| Compound of the present invention | 20 parts |
| Kaolin and synthetic high-dispersion silicic acid (volume ratio of 1:1) | 75 parts |
| Mixture of polyoxyethylene nonylphenyl ether and calcium alkylbenzene sulfonate | 5 parts |

The above ingredients are uniformly mixed and then pulverized to give a wettable powder formulation.

| Formulation Example 5 | |
|---|---|
| Compound of the present invention | 20 parts |
| Polyoxyethylene lauryl ether | 3 parts |
| Sodium dioctyl sulfosuccinate | 3.5 parts |
| Dimethyl sulfoxide | 37 parts |
| 2-Propanol | 36.5 parts |

The above ingredients are uniformly mixed for dissolution to give a water-soluble concentrate preparation.

| Formulation Example 6 | |
|---|---|
| Compound of the present invention | 2 parts |
| Dimethyl sulfoxide | 10 parts |
| 2-Propanol | 35 parts |
| Acetone | 53 parts |

The above ingredients are uniformly mixed for dissolution to give a solution for spraying.

| Formulation Example 7 | |
|---|---|
| Compound of the present invention | 5 parts |
| Hexylene glycol | 50 parts |
| Isopropanol | 45 parts |

The above ingredients are uniformly mixed for dissolution to give a solution for transdermal administration.

| Formulation Example 8 | |
|---|---|
| Compound of the present invention | 5 parts |
| Propylene glycol monomethyl ether | 50 parts |
| Dipropylene glycol | 45 parts |

The above ingredients are uniformly mixed for dissolution to give a solution for transdermal administration.

| Formulation Example 9 | |
|---|---|
| Compound of the present invention | 2 parts |
| Light liquid paraffin | 98 parts |

The above ingredients are uniformly mixed for dissolution to give a solution for transdermal (pour-on) administration.

| Formulation Example 10 | |
|---|---|
| Compound of the present invention | 2 parts |
| Light liquid paraffin | 58 parts |
| Olive oil | 30 parts |
| ODO-H (manufactured by Nisshin OilliO Group, Ltd.) | 9 parts |
| Shin-etsu silicone | 1 part |

The above ingredients are uniformly mixed for dissolution to give a solution for transdermal (pour-on) administration.

Test examples in connection with the present invention are shown below, but the present invention is not limited thereto.

Test Example 1

Test for control efficacy on *Myzus persicae*

Chinese cabbage plants were planted in plastic pots (diameter: 8 cm, height: 8 cm), Green peach aphids (*M. persicae*) were propagated on the plants, and the number of surviving Green peach aphids in each pot was counted. The sulfonamide group-containing condensed heterocyclic compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate} = 100 - \{(T \times Ca)/(Ta \times C)\} \times 100 \quad \text{[Math. 1]}$$

Ta: the number of survivors before the foliar application in a treatment plot

T: the number of survivors after the foliar application in a treatment plot

Ca: the number of survivors before the foliar application in a non-treatment plot C: the number of survivors after the foliar application in a non-treatment plot Criteria A: the control rate is 100%.

B: the control rate is 90 to 99%,

C: the control rate is 80 to 89%.

D: the control rate is 50 to 79%.

As a result, the compounds 1-1, 1-2, 1-3, 1-4, 1-5, 1-6, 1-7, 1-8, 1-9, 1-F101-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-4[7], 1-48, 1-491-50, 1-51, 1-52, 1-53, 1-54, 1-55, 1-56, 1-57, 1-58, 1-59, 1-60, 1-61, 1-621-63, 1-64, 1-65, 1-66, 1-67, 1-68, 1-69, 1-70, 1-71, 1-72, 1-73, 1-74, 1-75, 2-1, 2-2, 2-3, 2-4, 2-5, 2-6, 2-7, 2-8, 2-9, 2-10, 2-11,2-12,2-13,2-14,2-15, 2-16,3-1,3-2, 3-3, 3-4,3-5,4-1,4-2, 4-3,4-4,4-5,4-6,4-7,4-8, 4-9,4-10,4-11, 4-12, 4-13, 4-14, 4-15, 4-16, 4-17, 5-1, 5-2, 5-3, 5-4, 5-5, 5-6, 5-7, 5-8, 5-9, 5-10, 5-11, 5-12, 5-13, 5-14, 5-15, 5-16, 5-17, 5-18, 5-19, [5]-20, 6-1, 6-2, 7-1, 7-2, 7-3, 8-3, 8-4, 9-1, 9-2, 9-3, and 9-4 of the present invention showed the activity level evaluated as A.

Test Example 2

Insecticidal test on *Laodelphax* striatelius

The sulfonamide group-containing condensed heterocyclic compounds represented by the general formula (1) of the present invention or salts thereof were separately dispersed in water and diluted to 500 ppm. Rice plant seedlings (variety: Nihonbare) were dipped in the agrochenrical dispersions for 30 seconds. After air-dried, each seedling was put into a separate glass test tube and inoculated with ten 3rd-instar larvae of *L, striatellus*, and then the glass test tubes were capped with cotton plugs. At 8 days after the inoculation, the numbers of surviving larvae and dead larvae were counted to determine the survival rate, the corrected mortality rate was calculated according to the formula shown below, and the insecticidal efficacy was evaluated according to the criteria shown below.

$$\text{Corrected mortality rate (\%)} = 100\times(\text{Survival rate in a non-treatment plot} - \text{Survival rate in a treatment plot})/\text{Survival rate in a non-treatment plot} \quad \text{[Math. 2]}$$

Criteria

A: the corrected mortality rate is 100%.

B: the corrected mortality rate is 90 to 99%.

C: the corrected mortality rate is 80 to 89%.

D: the corrected mortality rate is 50 to 79%.

As a result, the compounds 1-1, 1-2, 1-3, 1-4, 1-5, 1-6, 1-7, 1-8, 1-9, 1-10, 1-11, 1-12, 1-13,1-14,1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75,2-1, 2-22-3, 2-4, 2-5,2-6.2-7, 2-8, 2-9,2-10,2-11,2-12,2-13,2-14, 2-15, 2-16, 3-1, 3-2, 3-3, 3-4, 3-5, 4-1, 4-2, 4-3, 4-4, 4-5, 4-6, 4-7, 4-8, 4-9, 4-10, 4-11, 4-12, 4-13, 4-14, 4-15,4-16, 4-17, 5-1, 5-2, 5-3, 5-4, 5-5, 5-6, 5-7, 5-8, 5-9, 5-10, 5-11, 5-12, 5-13, 5-14, 5-15, 5-16, 5-17, 5-18, 5-19, 5-20, 6-1, 6-2, 7-1, 7-2, 7-3, 8-3, 8-4, 9-1, 9-2, 9-3, and 9-4 of the present invention showed the activity level evaluated as A.

Test Example 3

Insecticidal test on *Plutella* xylostella

Adults of *P. xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different kind of sulfonamide group-containing condensed heterocyclic compound represented by the general formula (1) of the present invention or a salt thereof as an active ingredient. After air-dried, the seedlings were kept in a thermostatic chamber at 25° C. At 6 days after the dip treatment, the number of hatched larvae per plot was counted, the corrected mortality rate was calculated according to the formula shown below, and the insecticidal efficacy was evaluated according to the criteria of Test Example 2. This test was conducted in triplicate using 10 adults of P. xylostella per plot.

$$\text{Corrected Morality rate (\%)} = 100\times(\text{Number of hatched larvae in a non-treatment plot} - \text{Number of hatched larvae in a treatment plot})/\text{Number of hatched ; arvae in a non-treatment plot} \quad \text{[Math. 3]}$$

As a result, the compounds 1-1, 1-2, 1-3, 1-4, 1-5, 1-6, 1-7, 1-8, 1-9, 1-10, 1-11, 1-12, 1-13, 1-14, 1-15, 1-16, 1-17, 1-1& 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-371-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68. 1-69, 1-70, 1-71, 1-72, 1-73, 1-74, 1-75, 2-1, 2-2, 2-3, 2-4, 2-5, 2-6, 2-2-8, 2-9, 2-10, 2-11, 2-12, 2-13, 2-14, 2-15, 2-16, 3-1, 3-2, 3-3, 3-4, 3-5, 4-1, 4-2, 4-3, 4-4, 4-5, 4-6, 4-7, 4-8, 4-9, 4-10, 4-11,4-12,4-13,4-14, 4-15, 4-16, 4-17,5-1, 5-2, 5-3, 5-4, 5-5, 5-6,5-7,5-8, 5-9,5-10,5-11, 5-12, 5-13, 5-14, 5-15, 5-16, 5-17, 5-18, 5-195-20, 6-1, 6-2, 7-1, 7-2, 7-3, 8-3, 8-4, 9-1, 9-2, 9-3, and 9-4 of the present invention showed the activity level evaluated as A.

INDUSTRIAL APPLICABILITY

The compound of the present invention is highly effective in controlling a wide range of agricultural or horticultural pests, ectoparasites or endoparasites of animals (e.g., mites and ticks), etc. and thus is useful.

The invention claimed is:

1. A condensed heterocyclic compound having a sulfonamide group represented by the general formula (1):

(1)

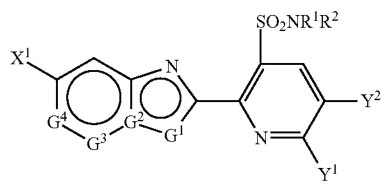

wherein $R^1$ and $R^2$ may be the same or different and each represent (a1) a hydrogen atom; or (a2) a ($C_1$-$C_6$) alkyl group; or (a3) $R^1$ and $R^2$ may join together to form a 3- to 6-membered aliphatic ring having the nitrogen atom of the sulfonamide group, $X^1$ represents (b1) a hydrogen atom;

(b2) a halo ($C_1$-$C_6$) alkyl group;

(b3) a halo ($C_1$-$C_6$) alkoxy group;

(b4) a halo ($C_1$-$C_6$) alkylthio group;

(b5) a halo ($C_1$-$C_6$) alkylsulfinyl group; or (b6) a halo ($C_1$-$C_6$) alkylsulfonyl group, $Y^1$ represents (c1) a hydrogen atom;

(c2) a halogen atom;

(c3) a ($C_1$-$C_6$) alkyl group;

(c4) a ($C_3$-$C_6$) cycloalkyl group;

(c5) a cyano ($C_3$-$C_6$) cycloalkyl group;

(c6) an aryl group;

(c7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group; or (c8) a triazole group, $Y^2$ represents (d1) a hydrogen atom;

(d2) a ($C_3$-$C_6$) cycloalkyl group;

(d3) a cyano ($C_3$-$C_6$) cycloalkyl group;

(d4) a halo ($C_1$-$C_6$) alkyl group;

(d5) a C ($R^3$)=$NOR^4$ group wherein $R^3$ represents a ($C_3$-$C_6$) cycloalkyl group, and $R^4$ represents a halo ($C_1$-$C_6$) alkyl group;

(d6) an aryl group;

(d7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, (m) a halo ($C_1$-$C_6$) alkylsulfonyl group, (k) a ($C_1$-$C_6$) alkylthio group, (1) a formyl group, (m) a ($C_1$-$C_6$) alkylcarbonyl group, (n) a ($C_1$-$C_6$) alkoxycarbonyl group, (o) an acetamide group, (p) a methylene dioxy group, and (q) a trimethylsilyl group;

(d8) $Y^1$ and $Y^2$ may join together with the pyridine ring bound to $Y^1$ and $Y^2$ to form an aromatic heterocyclic ring in which the aromatic ring moiety is an aromatic heterocyclic group optionally having, on the ring, 1 to 4 substituting groups selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d9) a halogen atom;

(d10) a ($C_1$-$C_6$) alkyl group;

(d11) a ($C_2$-$C_6$) alkenyl group;

(d12) a ($C_1$-$C_6$) alkoxy group;

(d13) a halo ($C_1$-$C_6$) alkoxy group;

(d14) a ($C_1$-$C_6$) alkylthio group;

(d15) a ($C_1$-$C_6$) alkylsulfonyl group;

(d16) a carboxyl group;

(d17) a ($C_1$-$C_6$) alkoxycarbonyl group;

(d18) a cyano ($C_1$-$C_6$) alkyl group;

(d19) a cyano halo ($C_1$-$C_6$) alkyl group;

(d20) a ($C_1$-$C_6$) alkoxy ($C_1$-$C_6$) alkyl group;

(d21) a ($C_1$-$C_6$) alkylsulfonyl ($C_1$-$C_6$) alkyl group;

(d22) an $NR^aR^b$ group wherein $R^a$ and $R^b$ may be the same or different and each represent (aa) a hydrogen atom, (ab) a ($C_1$-$C_6$) alkyl group, (ac) a ($C_2$-$C_6$) alkynyl group, (ad) a ($C_3$-$C_6$) cycloalkyl ($C_1$-$C_6$) alkyl group, (ae) a ($C_1$-$C_6$) alkoxy ($C_1$-$C_6$) alkyl group, (af) a ($C_1$-$C_6$) alkylcarbonyl group, (ag) a ($C_1$-$C_6$) alkoxycarbonyl group, or (ah) a dimethylaminocarbonyl group;

(d23) a $CONR^aR^b$ group wherein $R^a$ and $R^b$ are the same as above;

(d24) a dimethylamino ($C_1$-$C_6$) alkylideneamino group;

(d25) a dimethylsulfinylideneamino group;

(d26) a pyrimidyl group;

(d27) a pyrimidyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d28) a pyridyl group;

(d29) a pyridyl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d30) a pyridazinyl group;

(d31) a pyridazinyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d32) a pyrazinyl group;

(d33) a pyrazinyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d34) a furanyl group;

(d35) a furanyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d36) a thienyl group;

(d37) a thienyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d38) an imidazole group;

(d39) an imidazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d40) a pyrazole group;

(d41) a pyrazole group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d42) a thiazole group;

(d43) a thiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d44) an isothiazole group;

(d45) an isothiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d46) an oxazole group;

(d47) an oxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d48) an isoxazole group;

(d49) an isoxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d50) an oxadiazole group;

(d51) an oxadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d52) a thiadiazole group;

(d53) a thiadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d54) a triazole group;

(d55) a triazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d56) a pyrimidyloxy group;

(d57) a pyridyloxy group; or the following structural formula $Q^1$, $Q^2$, $Q^3$, $Q^4$, $Q^5$, or $Q_6$:

$Q^1$

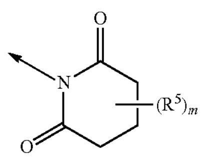

$Q^2$

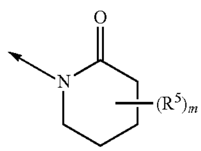

$Q^3$

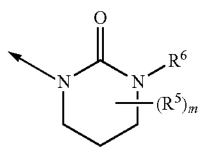

$Q^4$

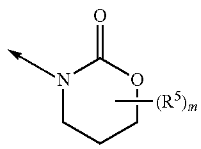

$Q^5$

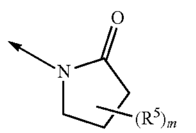

$Q^6$

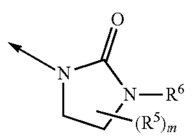

wherein $R^5$s may be the same or different and each represent a halogen atom or a ($C_1$-$C_6$) alkyl group; $R^6$ represents a ($C_1$-$C_6$) alkyl group; m represents an integer of 0 to 2, and the arrow represents a binding position, $G^1$ represents an oxygen atom, a nitrogen atom, CH, CF, or N—$CH_3$, $G^2$ represents a carbon atom or a nitrogen atom, $G^3$ represents a nitrogen atom or CH, and $G^4$ represents a nitrogen atom or a C—$X^2$ group, wherein $X^2$ represents a hydrogen atom or a halo ($C_1$-$C_6$) alkyl group, or a salt thereof.

2. The condensed heterocyclic compound having a sulfonamide group or the salt thereof according to claim 1, wherein $R^1$ and $R^2$ may be the same or different and each represent
(a1) a hydrogen atom; or
(a2) a ($C_1$-$C_6$) alkyl group; or
(a3) $R^1$ and $R^2$ may join together to form a 3- to 6-membered aliphatic ring having the nitrogen
atom of the sulfonamide group, $X^1$ represents
(b1) a hydrogen atom;
(b2) a halo ($C_1$-$C_6$) alkyl group;
(b3) a halo ($C_1$-$C_6$) alkoxy group;
(b4) a halo ($C_1$-$C_6$) alkylthio group;
(b5) a halo ($C_1$-$C_6$) alkylsulfinyl group; or
(b6) a halo ($C_1$-$C_6$) alkylsulfonyl group, $Y^1$ represents
(c1) a hydrogen atom;
(c2) a halogen atom;
(c3) a ($C_1$-$C_6$) alkyl group;
(c4) a ($C_3$-$C_6$) cycloalkyl group;
(c5) a cyano ($C_3$-$C_6$) cycloalkyl group;
(c7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group; or
(c8) a triazole group, $Y^2$ represents
(d1) a hydrogen atom;
(d2) a ($C_3$-$C_6$) cycloalkyl group;
(d3) a cyano ($C_3$-$C_6$) cycloalkyl group;
(d4) a halo ($C_1$-$C_6$) alkyl group;
(d5) a C ($R^3$)-NOR$^4$ group wherein $R^3$ represents a ($C_3$-$C_6$) cycloalkyl group, and $R^4$ represents a halo ($C_1$-$C_6$) alkyl group;
(d7) an aryl group having, on the ring, 1 to 5 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, (m) a halo ($C_1$-$C_6$) alkylsulfonyl group, (k) a ($C_1$-$C_6$) alkylthio group, (1) a formyl group, (m) a ($C_1$-$C_6$) alkylcarbonyl group, (n) a ($C_1$-$C_6$) alkoxycarbonyl group, (o) an acetamide group, (p) a methylene dioxy group, and (q) a trimethylsilyl group;
(d8) $Y^1$ and $Y^2$ may join together with the pyridine ring bound to $Y^1$ and $Y^2$ to form an aromatic heterocyclic ring in which the aromatic ring moiety is an aromatic heterocyclic group optionally having, on the ring, 1 to 4 substituting groups selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d9) a halogen atom;
(d10) a ($C_1$-$C_6$) alkyl group;
(d11) a ($C_2$-$C_6$) alkenyl group;
(d12) a ($C_1$-$C_6$) alkoxy group;
(d13) a halo ($C_1$-$C_6$) alkoxy group;
(d14) a ($C_1$-$C_6$) alkylthio group;
(d15) a ($C_1$-$C_6$) alkylsulfonyl group;
(d16) a carboxyl group;
(d17) a ($C_1$-$C_6$) alkoxycarbonyl group;
(d18) a cyano ($C_1$-$C_6$) alkyl group;
(d19) a cyano halo ($C_1$-$C_6$) alkyl group;
(d20) a ($C_1$-$C_6$) alkoxy ($C_1$-$C_6$) alkyl group;
(d21) a ($C_1$-$C_6$) alkylsulfonyl ($C_1$-$C_6$) alkyl group;
(d22) an $NR^aR^b$ group wherein $R^a$ and $R^b$ may be the same or different and each represent
(aa) a hydrogen atom,
(ab) a ($C_1$-$C_6$) alkyl group,
(ac) a ($C_2$-$C_6$) alkynyl group,
(ad) a ($C_3$-$C_6$) cycloalkyl ($C_1$-$C_6$) alkyl group,
(ae) a ($C_1$-$C_6$) alkoxy ($C_1$-$C_6$) alkyl group,
(af) a ($C_1$-$C_6$) alkylcarbonyl group,
(ag) a ($C_1$-$C_6$) alkoxycarbonyl group, or
(ah) a dimethylaminocarbonyl group;
(d23) a $CONR^aR^b$ group wherein $R^a$ and $R^b$ are the same as above;
(d24) a dimethylamino ($C_1$-$C_6$) alkylideneamino group;
(d25) a dimethylsulfinylideneamino group;
(d26) a pyrimidyl group;
(d27) a pyrimidyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d28) a pyridyl group;
(d29) a pyridyl group having, on the ring, 1 to 4 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d30) a pyridazinyl group;
(d31) a pyridazinyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d32) a pyrazinyl group;
(d33) a pyrazinyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d34) a furanyl group;
(d35) a furanyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d36) a thienyl group;
(d37) a thienyl group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d38) an imidazole group;
(d39) an imidazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d40) a pyrazole group;
(d41) a pyrazole group having, on the ring, 1 to 3 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d42) a thiazole group;
(d43) a thiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;
(d44) an isothiazole group;
(d45) an isothiazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$)

alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d46) an oxazole group;

(d47) an oxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d48) an isoxazole group;

(d49) an isoxazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d50) an oxadiazole group;

(d51) an oxadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d52) a thiadiazole group;

(d53) a thiadiazole group having, on the ring, one substituting group which may be the same or different and is selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d54) a triazole group;

(d55) a triazole group having, on the ring, 1 or 2 substituting groups which may be the same or different and are selected from (a) a halogen atom, (b) a cyano group, (c) a nitro group, (d) a ($C_1$-$C_6$) alkyl group, (e) a halo ($C_1$-$C_6$) alkyl group, (f) a ($C_1$-$C_6$) alkoxy group, (g) a halo ($C_1$-$C_6$) alkoxy group, (h) a ($C_1$-$C_6$) alkylthio group, (i) a halo ($C_1$-$C_6$) alkylthio group, (j) a ($C_1$-$C_6$) alkylsulfinyl group, (k) a halo ($C_1$-$C_6$) alkylsulfinyl group, (1) a ($C_1$-$C_6$) alkylsulfonyl group, and (m) a halo ($C_1$-$C_6$) alkylsulfonyl group;

(d56) a pyrimidyloxy group; or (d57) a pyridyloxy group, $R^5$s may be the same or different and each represent a halogen atom or a ($C_1$-$C_6$) alkyl group, $R^6$ represents a ($C_1$-$C_6$) alkyl group, m represents an integer of 0 to 2, $G^1$ represents an oxygen atom, a nitrogen atom, CH, or N—$CH_3$, $G^2$ represents a carbon atom or a nitrogen atom, $G^3$ represents a nitrogen atom or CH, and $G^4$ represents a nitrogen atom or a C—$X^2$ group wherein $X^2$ is the same as above.

3. The condensed heterocyclic compound having a sulfonamide group or the salt thereof according to claim 1, wherein $G^1$ represents N—$CH_3$, $G^2$ represents a carbon atom, $G^3$ represents a nitrogen atom, and $G^4$ represents a C—$X^2$ group wherein $X^2$ is the same as above.

4. The condensed heterocyclic compound having a sulfonamide group or the salt thereof according to claim 1, wherein $G^1$ represents a nitrogen atom, $G^2$ represents a carbon atom, and $G^3$ and $G^4$ each represent a nitrogen atom.

5. The condensed heterocyclic compound having a sulfonamide group or the salt thereof according to claim 1, wherein $G^1$ represents a nitrogen atom, $G^2$ represents a nitrogen atom, $G^3$ represents CH, and $G^4$ represents a C—$X^2$ group wherein $X^2$ is the same as above.

6. An agricultural or horticultural insecticide comprising the condensed heterocyclic compound having a sulfonamide group or the salt thereof according to claim 1 as an active ingredient.

7. A method for using an agricultural or horticultural insecticide, comprising treating plants or soil with an effective amount of the condensed heterocyclic compound having a sulfonamide group or the salt thereof according to claim 1.

8. An animal ectoparasite control agent comprising an effective amount of the condensed heterocyclic compound having a sulfonamide group or the salt thereof according to claim 1 as an active ingredient.

9. An animal endoparasite control agent comprising an effective amount of the condensed heterocyclic compound having a sulfonamide group or the salt thereof according to claim 1 as an active ingredient.

* * * * *